(12) United States Patent
Davis et al.

(10) Patent No.: US 8,263,035 B2
(45) Date of Patent: Sep. 11, 2012

(54) FORMING NANOPARTICLES IN BASIC AMINO ACID SOLS

(76) Inventors: Tracy M. Davis, Pinole, CA (US); Mark A. Snyder, St. Paul, MN (US); Michael Tsapatsis, Minneapolis, MN (US); J. Alex Lee, Minneapolis, MN (US)

(*) Notice: Subject to any disclaimer, the term of this patent is extended or adjusted under 35 U.S.C. 154(b) by 599 days.

(21) Appl. No.: 11/925,299

(22) Filed: Oct. 26, 2007

(65) Prior Publication Data

US 2008/0213883 A1 Sep. 4, 2008

Related U.S. Application Data

(60) Provisional application No. 60/854,539, filed on Oct. 26, 2006.

(51) Int. Cl.
*C01B 33/12* (2006.01)
*C01B 33/26* (2006.01)
(52) U.S. Cl. ............ 423/335; 423/327.1; 423/328.1; 423/330.1; 977/840; 977/722
(58) Field of Classification Search .................. None
See application file for complete search history.

(56) References Cited

U.S. PATENT DOCUMENTS 7,534,610 B1 * 5/2009 Kotov et al. ............... 435/402

OTHER PUBLICATIONS

Snyder, et al. (2007) Langmuir, 23: 9924-28.*
Baca, H.K., *Science*, 313 (2006) 337-341.
Belton, D., *Journal of Materials Chemistry*, 14 (2004) 2231-2241.
Bertazza, L., *Tetrahedron*, 62 (2006) 10434-10440.
Blanford, C. F., *Mater. Res. Soc. Symp. Proc.*, 549 (1999) 61-66.
Bohaty, A. K., *Langmuir*, 22 (2006) 5533-5536.
Brongersma, M. L., Langmuir, 22 (2006) 2856-2862.
Cebeci, F.C., Langmuir, 22 (2006) 2856-2862.
Cha, J.N. Nature, 403 (2000) 289-292.
Cheng, C. H. Journal of Physical Chemistry B, 109 (2005) 7266-7274.
Cichelli, J., Journal of the American Chemical Society, 128 (2006) 8130-8131.
Cousins, B. G., Journal of Materials Science: Materials in Medicine, 15 (2004) 355-359.
Davis, T. M., Nature Materials, 5 (2006) 400-408.
Davis, T. M., Chemistry of Materials, 18 (2006) 5814-5816.
Fedeyko, J. M., Journal of Physical Chemistry B, 108 (2004) 12271-12275.
Fedeyko, J. M., Langmuir, 21 (2005) 5197-5206.
Gemeinhart, R. A., Biotechnology Progress, 21 (2005) 532-537.
Graf, C., Langmuir, 18 (2002) 524-534.
Hawkins, K.M., Journal of American Chemical Society, 126 (2004) 9112-9119.
Hayes, R. A., Langmuir, 15 (1999) 2865-2870.
Holland, B. T., Chem. Mater., 11 (1999) 795-805.
Jan, J.-S., Chemistry of Materials, 17 (2005) 4310-4317.
Katelson, H. A., Langmuir, 12 (1996) 1134-1140.
Kroger, N., Science, 286 (1999) 1129-1132.
Kroger, N., Science, 298 (2002) 584-586.
Lee, D., Nano Letters, 6 (2006) 2305-2312.
Loo, C., Optics Letters, 30 (2005) 1012-1014.
Loo, C., Technology in Cancer Research & Treatment, 3 (2004) 33-40.
Loo, C., Nano Letters, 5 (2005) 709-711.
Melde, B. J., Chem. Mater, 14 (2002) 3326-3331.
Newton, M. R., Langmuir, 22 (2006) 4429-4432.
Nyffenegger, R., Journal of Colloid and Interface Science, 159 (1993) 150-157.
O'Neal, D. P., Cancer Letters, 209 (2004) 171-176.
Osseo-Asare, K., Colloids and Surfaces, 50 (1990) 321-339.
Ow, H, Nano Letters, 5 (2005) 113-117.
Prevo, B. G., Chemistry of Materials, 17 (2005) 3642-3651.
Rimer, J. D, Langmuir, 21 (2005) 8960-8971.
Rimer, J. D., Langmuir, 23 (2007) 2784-2791.
Rimer, J. D., J. Phys. Chem. B, 109 (2005) 12762-12771.
Rodriguez, F., Biomacromolecules, 5 (2004) 261-265.
Roy, I., Proceedings of the National Academy of Sciences, 102 (2005) 279-284.
Roy, I, Journal of the American Chemical Society, 125 (2003) 7860-7865.
Santra, S., Anal. Chem., 73 (2001) 4988-4993.
Schepelina, O., Langmuir, 22 (2006) 10523-10527.
Schoeman, B. J., Zeolites, 17 (1996) 447-456.
Snyder, M., A., Langmuir, 23 (2007) 9924-9928.
Stober, W., Journal of Colloid and Interface Science, 26 (1968) 62.
Sumper, M., Journal of Material Chemistry, 14 (2004) 2059-2065.
van Blaaderen, A., Journal of Colloid and Interface Science, 154 (1992) 481-501.
Wang, Z., Chem. Mater., 17 (2005) 6805-6813.
Yan, H, Adv. Mater., 11 (1999) 1003-1006.
Yan, H., Chem. Mater., 12 (2000) 1134-1141.
Yan, H., Chem. Mater., 13 (2001) 4314-4321.
Yan, H., Chem. Commun., 2000, 1477-1478.
Yancey, S. E., Journal of Applied Physics, 99 (2006) 034313.
Yang, S. Y., Chemistry of Materials, 16 (2004) 210-219.
Yang, S.-M., Small, 2 (2006) 458-475.
Yokoi, T., J. Amer. Chem. Soc., 128 (2006) 13664-13665.
Zhao, X., Advanced Materials, 16 (2004) 173-176.
Rouquerol, F. et al., "Adsorption by Powders & Porous Solids", Academic Press, pp. 288-289 (1999).
"Amino acid", pp. 1-18, from Wikipedia at http://en.wikipedia.org/wiki/Amino_acid (2010).

* cited by examiner

*Primary Examiner* — Robert M Kelly
(74) *Attorney, Agent, or Firm* — Fish & Richardson P.C.

(57) ABSTRACT

In general, in one aspect, the invention features a method that includes preparing a mixture comprising water, a basic amino acid, and a metal oxide precursor under conditions which result in the formation of metal oxide nanoparticles from the metal oxide precursor.

17 Claims, 22 Drawing Sheets

FORMING NANOPARTICLES IN BASIC AMINO ACID SOLS

CROSS-REFERENCE TO RELATED APPLICATIONS

This application claims priority to Provisional Patent Application No. 60/854,539, entitled "SILICA NANOPARTICLES IN BASIC AMINO ACID-SILICA SOLS" filed on Oct. 26, 2006, the entire contents of which are incorporated herein by reference.

TECHNICAL FIELD

This disclosure relates to Nanoparticle Suspensions, Films and Gels, and more particularly to Silica, Germania and Aluminosilicate Nanoparticles.

BACKGROUND

Conventional synthesis techniques of silica nanoparticles include the Stöber technique which is generally limited to monodisperse nanoparticles no smaller than approximately 30 nm, [Stober, W., et al., (1968) Journal of Colloid and Interface Science. 26, 62, Katelson, H. A., et al., (1996) Langmuir. 12, 1134-1140, van Blaaderen, A., et al., (1992) Journal of Colloid and Interface Science. 154, 481-501] Other methods aimed at achieving particle monodispersity in the 10 nm particle size range have been explored including more complex confined particle synthesis in reverse micelles (e.g., [Osseo-Asare, K., et al., (1990) Colloids and Surfaces. 50, 321-339]). Simultaneously controlling size and monodispersity of silica nanoparticles especially during the downsizing of particle scales to the 10 nm range has proven elusive especially by simple, benign synthesis techniques despite the prospect that such particles hold for surmounting limitations of scale associated with particle-based and thin-film technologies.

SUMMARY

The techniques disclosed herein employ a benign and facile approach to synthesize silica and other metal oxide (e.g., germania) nanoparticles of controlled size (c.a., 4 nm to more than 25 nm in diameter) in aqueous solutions of lysine, a renewable chemical, and other basic amino acids (e.g., arginine). As used herein, nanoparticles refer to particles which have a maximum dimension of 30 nm or less (e.g., 25 nm or less, 20 nm or less, 15 nm or less, 14 nm or less, 12 nm or less, 10 nm or less, 8 nm or less, 7 nm or less, 6 nm or less, 5 nm or less, 4 nm or less). For example, spherical nanoparticles have a diameter of 30 nm or less. In embodiments, metal oxide nanoparticles are synthesized from simple solutions composed only of water, a basic amino acid (e.g., lysine), and a complementary precursor metal ethoxide (e.g., tetraethylorthosilicate, TEOS). Buffered by the amino acid itself, the synthesis occurs at moderately basic to near-neutral conditions, eliminating the need for addition of buffering agents and/or more complex hydrolytic molecules.

In general, in a first aspect, the invention features a method that includes preparing a mixture comprising water, a basic amino acid, and a metal oxide precursor under conditions which result in the formation of metal oxide nanoparticles from the metal oxide precursor.

Implementations of the method can include one or more of the following features and/or features of other aspects. For example, the metal oxide nanoparticles can have an average maximum dimension of 12 nm or less (e.g., 10 nm or less, 5 nm or less). The metal oxide nanoparticles can have a standard deviation in maximum dimension of 15% or less (e.g., 12% or less, 10% or less, 8% or less, 6% or less, 5% or less, 4% or less).

The conditions can include maintaining the mixture at a temperature of 100° C. or less (e.g., 75° C. or less, 60° C. or less, 50° C. or less, 40° C. or less, 30° C. or less, 25° C. or less) during formation of the metal oxide nanoparticles. The conditions can include stirring or agitating the mixture for one hour or more during formation of the metal oxide nanoparticles. The stirring rate can be determined to provide metal oxide nanoparticles of a desired size.

The metal oxide nanoparticles can be silica nanoparticles, germania nanoparticles or alumino-silicate nanoparticles. The metal oxide precursor can undergo a hydrolysis reaction during formation of the metal oxide nanoparticles.

The mixture can have a pH of 11 or less (e.g., 10 or less, 9 or less, 8 or less).

The basic amino acid can be lysine or arginine. The lysine or arginine content can be determined to provide metal oxide nanoparticles of a desired size.

The metal oxide precursor can be a silica precursor, such as TEOS.

The water can include deuterated water. Relative concentrations of deuterated water and water can be determined to provide metal oxide nanoparticles of a desired size.

The method can further include forming a gel that includes the metal oxide nanoparticles. The gel can be formed by adding poly peptide to the sol. The poly peptide can be di-lysine (i.e., Lysine-Lysine).

The method can include encapsulating living cells using the metal oxide nanoparticles. The cells and growth medium (e.g., nutrients for the cells) can be first added to the sol. The cells can be mammalian cells.

In some embodiment, the method includes casting a film comprising the metal oxide nanoparticles on a support.

In another aspect, the invention features a method that includes providing a solution comprising a basic amino acid, adding a compound to the solution, wherein the addition of the compound forms silica nanoparticles in the solution.

Implementations of the method can include one or more of the following features and/or features of other aspects. For example, the basic amino acid can be lysine or arginine.

The solution can be an aqueous solution. The solution can be a basic solution. The solution can have a pH of about 11 or less (e.g., about 10 or less). In some embodiments, the solution pH does not exceed about 11 while the compound is added to the solution and the silica nanoparticles form in the solution. The solution containing the formed silica nanoparticles can have a pH of about 10 or less (e.g., about 9 or less, about 8 or less).

The solution can include an alcohol, such as ethanol. Preparing the solution can include adding the basic amino acid to water. The amount of the amino acid added can be less than 20% (e.g., less than 15%, less than 12%, less than 10%) of its solubility in water. In certain embodiments, the amount of the amino acid added is less than 50% of its solubility in water. In some embodiments, the amount of the amino acid added is less than 90% of its solubility in water. In certain embodiments, the amount of the amino acid added is less than 100% of its solubility in water. Alternatively, in some embodiments, the amount of the amino acid added exceeds its solubility in water (e.g., by 10% or more, by 20% or more, by 30% or more).

The compound can be a silica precursor, such as tetraethylorthosilicate. The compound can undergo a chemical reaction, e.g., hydrolysis, in the solution to provide silica.

The silica nanoparticles can have maximum dimension of about 30 nm or less (e.g., about 20 nm or less, about 15 nm or less, about 12 nm or less, about 10 nm or less, about 8 nm or less, about 6 nm or less, about 5 nm or less, about 4 nm or less).

The silica nanoparticles can have a narrow particle size distribution. For example, the particle size distribution can be such that the standard deviation from the average diameter is no more than 20% (e.g., 15% or less, 12% or less, 10% or less, 8% or less, 7% or less, 6% or less, 5% or less).

The silica nanoparticles can have a maximum dimension in a range from about 4 nm to about 30 nm (e.g., about 5 nm to about 15 nm, about 5 nm to about 9 nm).

The basic amino acid and the compound can be added to the solution in concentrations determined to provide silica nanoparticles of a desired size. The basic amino acid and the compound can be added to the solution and then mixed by stirring and/or sonication. The mixing rate and conditions (e.g., temperature) can be determined to provide silica nanoparticles of a desired size.

The solution can include heavy water (i.e., deuterium oxide) and water. The relative concentrations of heavy water and water can be determined to provide silica nanoparticles of a desired size.

The method can include forming a clear gel comprising the silica nanoparticles. The gel can be formed by the addition of a peptide to the solution containing the silica nanoparticles. The gel can be formed by the addition of a di-peptide to the solution containing the silica nanoparticles. The di-peptide can be di-lysine (Lysine-Lysine). The gel can be formed after the addition of a cell growth medium. The method can also include the addition of a cell growth medium before the formation of the gel.

In some embodiments, the method includes encapsulating living cells using the silica nanoparticles. The cells can be islets. The cells can be human umbilical vein endothelial cells. Cells can be added before the formation of the gel. A cell growth medium can be added before or with the cells. The cell growth medium can be added before the formation of the gel.

The method can include casting a film comprising the silica nanoparticles on a support. The film can be deposited on a non porous support. The nonporous support can be a silicon wafer or a glass (e.g., a silicate glass). The film can be deposited on or inside a porous support. The porous support can be porous stainless steel or porous alumina. The film can be continuous (e.g., a continuous monolayer or continuous multilayer film). In some embodiments, the film is a continuous closed packed monolayer or continuous closed packed multilayer film. In certain embodiments, the film is discontinuous and include of bands of nanoparticles. The bands can be regularly spaced.

The film can be deposited by immersing the support in a bath containing the solution that contains the silica nanoparticles, withdrawing the support at a constant speed while directing the flow of a gas stream parallel to the support. The nanoparticle concentration, withdrawal speed and gas flow rate can be determined to provide a continuous coating with a desired thickness. The nanoparticle concentration, withdrawal speed and gas flow rate can be determined to provide a discontinuous coating with desired band width and spacing. The bands can be parallel or perpendicular to the withdrawal direction.

The method can include bringing in contact the supported silica nanoparticle film with a medium containing living cells. Living cells can attach preferentially on the areas of the support that are not covered by a silica nanoparticle deposit.

The method can include adding a germania precursor or an alumina precursor.

In another aspect, the invention features a gas or liquid separation membrane prepared using the methods disclosed herein.

In general, in another aspect, the invention features a method that includes providing a solution that includes a basic amino acid, and adding a compound to the solution, wherein the addition of the compound forms germania nanoparticles or alumina nanoparticles in the solution. Implementations of the method can include one or more of the features discussed above. In some embodiments, a reactive silicate no sooner exceeds the aqueous solubility limit of silica than rapid formation of silica nanoparticles is detected [see, e.g., Davis, T. M., et al., (2006) Chemistry of Materials. 18, 5814-5816]. The size and shape of these nanoparticles can be tuned by a wide range of handles including, for example, 1) the temperature at which the metal ethoxide is hydrolyzed, 2) the temperature at which the hydrolyzed sol is aged, 3) the molar composition of the metal ethoxide in the synthesis solution, 4) the pH of the synthesis solution governed by the molar amino acid content, 5) the rate at which the solution is homogenized during hydrolysis, and/or even 6) the fraction of the solvent (water) that is deuterated.

In certain embodiments, the silica nanoparticles prepared by these means display colloidal and structural stability in solution and, especially for those prepared at elevated temperatures, when isolated by evaporative drying or dialysis [see, e.g., Snyder, M. A., et al., (2007) Langmuir. 23, 9924-9928]. Facile ordering of the produced nanoparticles into nanoparticle crystals both in situ and ex situ is possible without addition of any structure directing agents to the synthesized sols. In addition, multi- and monolayer locally ordered nanoparticle coatings have been realized from the nanoparticle sols via conventional and novel dip-coatings methods [see, e.g., Snyder, M. A., et al., (2007) Langmuir. 23, 9924-9928]. Embodiments of nanoparticle assembly can include routes to clear metal oxide gels with tunable porosity and morphology by, for example, either ageing of dialyzed sols or by addition only of compatible peptide oligomers (e.g., di-lysine) [see, e.g., Davis, T. M., et al., (2006) Chemistry of Materials. 18, 5814-5816]. These gels can be used for the encapsulation of living cells.

This facile and benign approach to synthesis of highly monodisperse and size-tunable silica nanoparticles, and more generally other metal oxides, stands to impact a broad range of fields including colloidal membrane technology [see, e.g., Cichelli, J., et al., (2006) Journal of the American Chemical Society. 128, 8130-8131, Schepelina, O., et al., (2006) Langmuir. 22, 10523-10527, Newton, M. R., et al., (2006) Langmuir. 22, 4429-4432, Bohaty, A. K., et al., (2006) Langmuir. 22, 5533-5536], colloidal lithography [see, e.g., Yang, S.-M., et al., (2006) Small. 2, 458-475], cancer therapeutics and diagnostics [see, e.g., Brongersma, M. L., (2003) Nature Materials. 2, 296-297, Loo, C., et al., (2005) Optics Letters. 30, 1012-1014, Loo, C., et al., (2004) Technology in Cancer Research & Treatment. 3, 33-40, Loo, C., et al., (2005) Nano Letters. 5, 709-711, ONeal, D. P., et al., (2004) Cancer Letters. 209, 171-176], photonics [see, e.g., Graf, C., et al., (2002) Langmuir. 18, 524-534], drug and/or DNA delivery [see, e.g., Gemeinhart, R. A., et al., (2005) Biotechnology Progress. 21, 532-537, Roy, I., et al., (2005) Proceedings of the National Academy of Sciences. 102, 279-284, Roy, I., et al., (2003) Journal of the American Chemical Society. 125, 7860-7865], ultrasensitive bioanalysis [see, e.g., Bertazza, L., et al., (2006) Tetrahedron. 62, 10434-10440, Nyffenegger, R., et al., (1993) Journal of Colloid and Interface Science. 159, 150-157, Ow, H., et al., (2005) Nano Letters. 5, 113-117, Santra, S., et al., (2001) Anal. Chem. 73, 4988-4993, Zhao, X., et al., (2004) Advanced Materials. 16, 173-176], and coatings technology (e.g., antifog, anti-reflection) [see, e.g., Cebeci, F. C., et al., (2006) Langmuir. 22, 2856-2862, Hayes, R. A., et al., (1999) Langmuir. 15, 2865-2870, Lee, D., et al., (2006) Nano Letters. 6, 2305-2312, Prevo, B. G., et al., (2005) Chemistry of Materials. 17, 3642-3651, Yancey, S. E., et al., (2006) Journal of Applied Physics. 99, 034313].

The details of one or more embodiments of the invention are set forth in the accompanying drawings and the description below. Other features and advantages of the invention will be apparent from the description and drawings, and from the claims.

DETAILED DESCRIPTION

Figure 1:
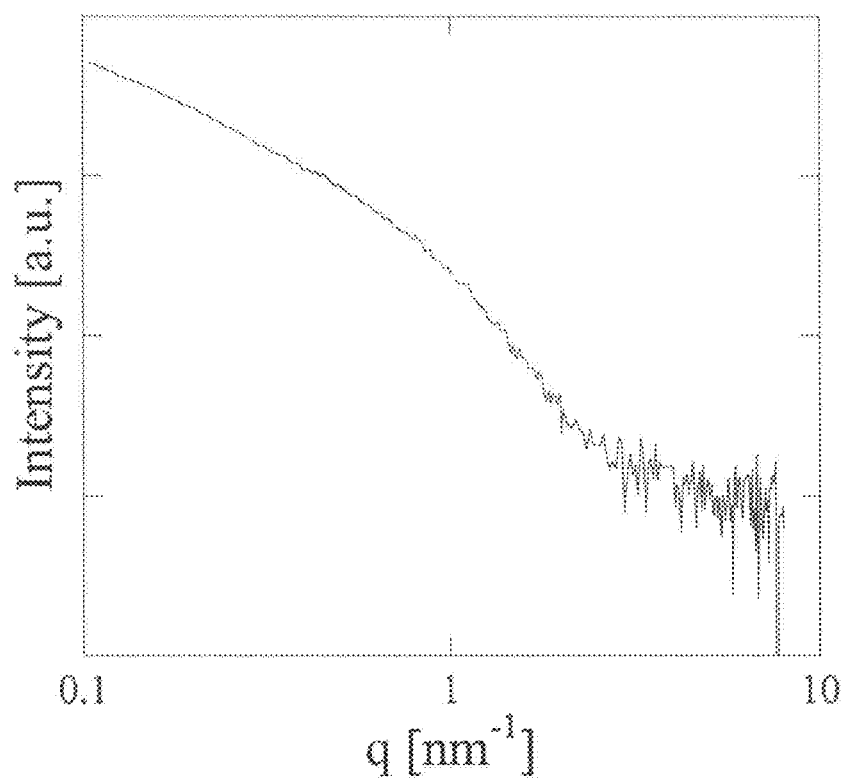
FIG. 1 is the small-angle x-ray scattering (SAXS) pattern for a polydisperse population of silica nanoparticles prepared through hydrolysis of tetraethylorthosilicate (TEOS, 98% Aldrich) in distilled water with no additional hydrolytic agents.

Applicants have demonstrated that that TEOS hydrolysis can and does occur in pure water at near-neutral pH without any additional agents, as described, for example, in EXAMPLE 1, infra. The result of such hydrolysis, however, is a polydisperse population (ca., 10-100 nm) of unstable silica nanoparticles that form disordered nanoparticle aggregates in situ and lead to the eventual transformation of the sol to a loose, clear gel (see, e.g., EXAMPLE 2, infra).

Pure hydrolytic agents are identified herein, which, when added to mixtures of water and metal ethoxide precursors, results in metal oxide nanoparticles at near neutral pH that 1) are highly monodisperse (e.g., standard deviation in particle diameter can be 15% or less, 14% or less, 12% or less, 11% or less, 10% or less, 8% or less, 5% or less), 2) exhibit colloidal and structural stability, and 3) can be tuned to average sizes (e.g., average maximum particle dimension, such as the particle's diameter for substantially spherical particles) on the order of 10 nm or less (e.g., 9 nm or less, 8 nm or less, 7 nm or less, 6 nm or less, 5 nm or less, 4 nm or less).

Previously, Stöber [see, e.g., Stober, W., et al., (1968) Journal of Colloid and Interface Science. 26, 62] has proposed a process capable of silica condensation into stable and monodisperse silica nanoparticles ranging in size from hundreds of nanometers to as small as 30 nm. In this commonly employed approach of the previous art, slow hydrolysis of TEOS is catalyzed by a strong base (e.g., ammonium hydroxide) in alcoholic solutions and in the presence of controlled amounts of water. Hydrolysis of TEOS in the presence of highly basic alkylammonium cations during standard zeolite synthesis has also been shown to lead to the formation of silica nanoparticles (ca. 4 nm) in highly alkaline solutions [see, e.g., Cheng, C. H., et al., (2005) Journal of Physical Chemistry B. 109, 7266-7274, Fedeyko, J. M., et al., (2004) Journal of Physical Chemistry B. 108, 12271-12275, Fedeyko, J. M., et al., (2005) Langmuir. 21, 5197-5206, Rimer, J. D., et al., (2005) Langmuir. 21, 8960-8971, Schoeman, B. J., et al., (1996) Zeolites. 17, 447-456, Yang, S. Y., et al., (2004) Chemistry of Materials. 16, 210-219].

Biomimetic pathways to silica formation present an attractive and theoretically more benign route to silica condensation given the well-documented phenomenon of biomineralization occurring in plants, sponges, and diatoms in nature under physiological conditions [see, e.g., Kroger, N. et al., (1999) Science. 286, 1129-1132; Cha, J. N. et al., (2000) Nature. 403, 289-292; Kroger, N. et al., (2002) Science. 298, 584-586; Sumper, M. and Kroger, N., (2004) Journal of Material Chemistry. 14, 2059-2065; Hawkins, K. M. et al., (2004) Journal of American Chemical Society. 126, 9112-9119; Jan, J.-S. et al., (2005) Chemistry of Materials. 17, 4310-4317; Belton, D. et al., (2004) Journal of Materials Chemistry. 14, 2231-2241; Rodriguez, F. et al., (2004) Biomacromolecules. 5, 261-265; Baca, H. K. et al., (2006) Science. 313, 337-341]. In particular, studies of biomineralization routes have all focused on harnessing the hydrolytic functionality of large poly-peptides in lieu of the highly basic agents employed in Stöber and other synthesis routes. Specifically, Cha et al. [see, e.g., Cha, J. N. et al., (2000) Nature. 403, 289-292] showed that large (ca. 100 μm) polydisperse silica particles could be synthesized using cysteine-lysine block copolypeptides as effective mimics of silicatein properties. Kröger et al. [see, e.g., Kroger, N. et al., (1999) Science. 286, 1129-1132] showed that silaffins (polycationic peptides) isolated from diatom cell walls can be employed for rapid and benign synthesis of silica nanospheres on the order of 50 nm in diameter.

The aqueous solution of only amino acids and metal ethoxides disclosed herein offers a surprisingly simple approach (e.g., without addition of complex poly-peptides, buffering agents, organics, or highly basic components) to achieve monodisperse silica nanoparticles as small as 4 nm in diameter at room temperature and more benign pH values ranging from 10 to near-neutral conditions (e.g., about 9 or less, about 8 or less, about 7)(see, e.g., EXAMPLE 3, infra). The attractiveness of this approach is further underscored by the identified nature of lysine as a renewable chemical [see, e.g., Werpy T. and G. Petersen, Editors. (2004) Top Value Added Chemicals from Biomass. Volume I—Results of Screening for Potential Candidates from Sugars and Synthesis Gas. Produced by the Staff at Pacific Northwest National Laboratory (PNNL), National Renewable Energy Laboratory (NREL), Office of Biomass Program (EERE). For the Office of the Biomass Program].

Ultimately, the ability to synthesize metal oxide particles on the order of 10 nm or smaller is critical for overcoming limitations of scale associated with the downsizing of devices and applications. While, the conventional Stöber process is a recognized and widely practiced route to monodisperse silica nanoparticles of hundreds of nanometers in size, persistent monodispersity has been reported only for particles as small as 30 nm. Attempts to employ this process to produce smaller nanoparticles have been plagued by both polydispersity and colloidal instability (i.e., aggregation).

In fact, even when small (ca. 4 nm) silica nanoparticles have been synthesized, for instance through hydrolysis of TEOS in the presence of alkylammonium cations [see, e.g., Cheng, C. H., et al., (2005) Journal of Physical Chemistry B. 109, 7266-7274, Fedeyko, J. M., et al., (2004) Journal of Physical Chemistry B. 108, 12271-12275, Fedeyko, J. M., et al., (2005) Langmuir. 21, 5197-5206, Rimer, J. D., et al., (2005) Langmuir. 21, 8960-8971, Schoeman, B. J., et al., (1996) Zeolites. 17, 447-456, Yang, S. Y., et al., (2004) Chemistry of Materials. 16, 210-219], they have been shown to evolve in their colloidal stability upon ageing [see, e.g., Davis, T. M., et al., (2006) Nature Materials. 5, 400-408], leading eventually to aggregative growth of complex zeolite structures. Moreover, despite the wealth of reports on biomineralization, none have produced conclusive evidence of stable nanoparticles in the size range of 10 nm or less. In fact, in addition to the relatively large size (ca. 50 nm) of the silica nanoparticles identified by Kröger et al. [see, e.g., Kroger, N. et al., (1999) Science. 286, 1129-1132], colloidal instability of the nanoparticles lead in that case to their association into networks of nanospheres.

Confined synthesis of silica nanoparticles in reverse micelle systems (see, e.g., [Osseo-Asare, K., et al., (1990) Colloids and Surfaces. 50, 321-339]) has also been pursued, enabling finer control of stable nanoparticle size in the sub 30 nm range. While that process enables control of particle size as well as particle stability, it is limited by its complexity.

It is, therefore, surprising that the simple method disclosed herein of TEOS hydrolysis in aqueous amino acid solutions, is capable of producing highly monodisperse silica nanoparticles in the sub-30 nm range at room temperature (see, e.g., EXAMPLE 3, infra) that exhibit colloidal stability over time scales exceeding months. The colloidal stability in these systems has been confirmed by SAXS and cryo-TEM, which both highlight isolated nanoparticles in solution in lieu of particle aggregates in both fresh and aged sols.

The ability to finely tune the size of particles on the order of 10 nm in size is ultimately critical for realization of many of the aforementioned applications of silica nanoparticles. While 4 nm particles have been identified in highly basic zeolite synthesis solutions [see, e.g., Cheng, C. H., et al., (2005) Journal of Physical Chemistry B. 109, 7266-7274, Fedeyko, J. M., et al., (2004) Journal of Physical Chemistry B. 108, 12271-12275, Fedeyko, J. M., et al., (2005) Langmuir. 21, 5197-5206, Rimer, J. D., et al., (2005) Langmuir. 21, 8960-8971, Schoeman, B. J., et al., (1996) Zeolites. 17, 447-456, Yang, S. Y., et al., (2004) Chemistry of Materials. 16, 210-219], no means have been derived for gross particle size adjustment after they are formed. Namely, for that system it has been shown that increasing silica content serves only to increase the number density of the particles while particle size remains constant. Furthermore, the nanoparticles formed therein are relatively insensitive to synthesis conditions such as temperature, sol homogeneity (i.e., stirring), and changes in alkylammonium content [see, e.g., Fedeyko, J. M., et al., (2004) Journal of Physical Chemistry B. 108, 12271-12275]. Rather, onset of the formation of consistently sized nanoparticles seems more strongly linked simply to conditions that lead the system to surpass the silica solubility limit.

In the biomimetic system described by Yokoi et al. [see, e.g., J. Amer. Chem. Soc., 128 (2006)], the authors speculate that 1) lysine serves to impart "size control of the silica nanospheres because L-lysine molecules can cover the nanosphere surface in the growth process", 2) "the size of the silica nanosphere was slightly increased with an increase in the proportion of octane in the solvent," and 3) mixtures of lysine stereoisomers may pack less efficiently on the silica nanoparticle surface leading to larger particles.

In light of the limited particle size control possible in highly basic alkylammonium systems and the mere speculation of such for biomimetic systems employing organics and pH buffering, the wide range of confirmed handles available for tuning particle size in the simpler method disclosed herein is surprising. Examples of variables for tuning particle size include silica content (see, e.g., EXAMPLE 4, infra), synthesis and ageing temperatures (see, e.g., EXAMPLES 5-6, infra), degree of sol homogenization during hydrolysis (see, e.g., EXAMPLE 8, infra), sol pH and/or amino acid content (see, e.g., EXAMPLE 9, infra), and even the fractional deuteration of the aqueous solvent (see, e.g., EXAMPLE 10, infra).

For example, silica content can be in a range from 7.5 mM to 2 M (e.g., from 1.8 M to 10 mM, from 1 M to 0.1 M, from 0.3 M to 0.1 M) In some embodiments, silica content can be about 10 mM or more (e.g., about 40 mM or more, about 0.1 M or more, about 0.3 M or more, about 1 M or more). In certain embodiments, silica content can be about 1.8 M or less (e.g., about 1 M or less, about 0.3 M or less, about 0.1 M or less). It is believed that higher silica content can lead to larger particle size.

Specifically, in some embodiments, particle size is initially insensitive to increasing silica content (see, e.g., EXAMPLE 3, infra) similar to the alkylammonium-derived silica nanoparticles. However, particle size can become highly sensitive to further increases in silica content (see, e.g., EXAMPLE 4, infra) well above the silica solubility limit, resulting in increases in particle size.

In certain embodiments, particle size is also sensitive to the temperature at which hydrolysis is carried out (see, e.g., EXAMPLE 5, infra). Namely, for a given composition of the reaction solution, particle size is observed to generally increase with increasing hydrolysis temperature.

For example, hydrolysis temperature can be in a range from 25° C. to 80° C. (e.g., from 25° C. to 70° C., from 25° C. to 60° C., from 40° C. to 60° C., from 55° C. to 65° C.). In some embodiments, hydrolysis temperature can be about 25° C. or more (e.g., about 30° C. or more, about 40° C. or more, about 60° C. or more). In certain embodiments, hydrolysis temperature can be about 80° C. or less (e.g., about 70° C. or less, about 60° C. or less, about 50° C. or less). It is believed that higher hydrolysis temperature can lead to larger particle size.

In certain embodiments, the size and morphology of silica nanoparticles can be further tuned following completion of the hydrolysis (i.e., formation of the nanoparticles) by subsequent ageing of the sols at elevated temperatures (see, e.g., EXAMPLE 6, infra). Under such conditions, nanoparticles are observed to increase in size with increasing ageing temperature, and become more spherical (i.e., perfected).

For example, hydrothermal ageing temperature can be in a range from 25° C. to 100° C. (e.g., from 25° C. to 80° C., from 25° C. to 60° C., from 60° C. to 100° C., from 80° C. to 100° C.). In some embodiments, hydrothermal ageing temperature can be about 25° C. or more (e.g., about 40° C. or more, about 60° C. or more, about 80° C. or more). In certain embodiments, hydrothermal ageing temperature can be about 100° C. or less (e.g, about 80° C. or less, about 60° C. or less, about 40° C. or less). It is believed that higher hydrothermal ageing temperature can lead to larger particle size and more spherical morphology.

In addition, in light of the challenges associated with the previous art for obtaining monodisperse nanoparticles on the order of 10 nm in diameter, a surprising result is the high degree of particle monodispersity that is possible with the simple synthesis disclosed herein. Quantification of this monodispersity has been carried out in a number of ways. The secondary maxima (marked by '*') in the SAXS patterns for representative sols of EXAMPLE 6, infra, (FIG. 7) is indicative of a high degree of particle monodispersity. As disclosed in EXAMPLE 7, infra, additional and consistent quantification of this monodispersity is possible through collection of particle measurement statistics directly from cryo-TEM imaged nanoparticles of EXAMPLES 3-6, infra, yielding a maximum standard deviation in the particle diameter of only 11%.

In some embodiments, nanoparticle size can be sensitive (see, e.g., EXAMPLE 8, infra) to the degree of sol homogenization during hydrolysis especially at higher temperatures. Namely, particle size is observed in some cases to more than double as a result of efficient versus poor sol homogenization (i.e., slow versus fast stir rates).

For example, stirring rates can be in a range from 0 to 1250 rpm (e.g., from 0 to 1000 rpm, from 500 to 800 rpm, from 750 to 850 rpm, from 1000 to 1250 rpm). In some embodiments, stirring rates can be about 500 rpm or more (e.g., about 750 rpm or more, about 800 rpm or more, about 1000 rpm or more). In certain embodiments, stirring rates can be about 1000 rpm or less (e.g, about 800 rpm or less, about 750 rpm or less, about 500 rpm or less). It is believed that higher stirring rate can lead to smaller particle size.

A feature of certain embodiments, such as the lysine-silica system, is the ability to tune particle size based on sol pH as described, for example, in EXAMPLE 9, infra.

For example, sol pH can be in a range from 8.5 to 10.2 (e.g., from 8.5 to 10, from 9 to 10, from 9.5 to 10, from 10 to 10.2) In some embodiments, sol pH can be about 8.5 or more (e.g., about 9 or more, about 9.5 or more, about 10 or more). In certain embodiments, sol pH can be about 10 or less (e.g, about 9.8 or less, about 9.5 or less, about 9 or less). It is believed that lower sol pH can lead to larger particle size.

The sol pH can be simply adjusted by tuning the concentration of the amino acid employed in the synthesis without introducing any new acidic, basic, or buffering agents or organic additives like those commonly employed in biomineralization. Generally, the nanoparticle size increases with decreasing pH (decreasing basic amino acid content).

For example, lysine content can be in a range from 0.2 mM to 50 mM (e.g., from 1 mM to 20 mM, from 20 mM to 40 mM, from 40 mM to 50 mM, from 0.2 mM to 1 mM) In some embodiments, lysine content can be about 0.2 mM or more (e.g., about 1 mM or more, about 10 mM or more, about 30 mM or more). In certain embodiments, lysine content can be about 50 mM or less (e.g, about 40 mM or less, about 20 mM or less, about 10 mM or less). It is believed that lower lysine content can lead to larger particle size.

Preparation of Alkylammonium-Derived Silica Nanoparticles in Fractionally deuterated aqueous solutions [see, e.g., Rimer, J. D., et al., (2005) J. Phys. Chem. B. 109, 12762-12771] has resulted in constant particle size, enabling contrast matching studies to be carried out during SANS analysis. Contrary to the alkylammonium system, an unexpected handle for fine control of particle size in the case of the disclosed invention is afforded by the fraction of deuterated water molecules in the reaction mixture (see, e.g., EXAMPLE 10, infra). In particular, in certain embodiments, as the aqueous component of the reaction mixture becomes more deuterated in the simple system of lysine, silica, and water, the size of the nanoparticles is observed to increase.

For example, $D_2O$ content can be in a range from 0 to 100% m/m (e.g., from 5 to 100% m/m, from 20 to 100% m/m, from 50 to 100% m/m, from 75 to 100% m/m) In some embodiments, $D_2O$ content can be about 5% m/m or more (e.g., about 20% m/m or more, about 50% m/m or more, about 75% m/m or more). In certain embodiments, $D_2O$ content can be about 100% m/m or less (e.g, about 75% m/m or less, about 50% m/m or less, about 25% m/m or less). It is believed that higher $D_2O$ content can lead to smaller particle size.

In addition to isolated, stable silica nanoparticles, the ability to direct the association and assembly of these particles may prove important for new materials applications. Yokoi et al. [see, e.g., J. Amer. Chem. Soc., 128 (2006)] have highlighted how silica nanoparticles synthesized through TEOS hydrolysis in water, lysine, and octane and buffered to a pH of 9.2 form colloidal crystals of 1-3 μm following high-temperature drying. Drying of commercial nanoparticle sols (e.g., Snowtex-XS®, Nissan Chemical) consisting, according to manufactures' specifications, of 7 nm silica nanoparticles in aqueous solutions, result in disordered particle aggregates rather than ordered colloidal crystals.

In some embodiments (see, e.g., EXAMPLE 11, infra), colloidal crystals of silica nanoparticles are formed upon room temperature evaporative drying of the nanoparticle sol composed only of water and, e.g., lysine without further pH buffering and in the absence of any organic. In fact, the extent of ordering occurs over scales of more than 10 μm in this simple system, further distinguishing it from more complex methods of Yokoi et al. [J. Amer. Chem. Soc., 128 (2006)] and underscoring its versatility in comparison to commercially available silica sols. In addition to the ex situ synthesis of large colloidal crystals described, for example, in EXAMPLE 11, infra, facile in situ assembly of the silica nanoparticles near fixed boundaries (e.g., near the carbon skeleton of TEM grids) is also observed via cryo-TEM (see, e.g. EXAMPLE 12, infra).

Such facile nanoparticle ordering, especially when achieved with size-tunable nanoparticles, has potential implications in the fields of protective coatings, selective membranes, nano-lithography, and others. In some embodiments (see, e.g., EXAMPLE 13, infra), a coating device described in [Snyder, M. A., et al., (2007) Langmuir. 23, 9924-9928] and the example that combines conventional dip-coating with evaporation induced self-assembly has been employed to prepare multi- and near monolayer films that display local nanoparticle ordering using the silica nanoparticle sols described herein. Adjustment of coating and evaporation rates enables control of coating thickness (i.e., number of layers). In certain embodiments (see, e.g., EXAMPLE 14, infra), quasi-periodic patterning of banded silica nanoparticle coatings can be achieved. Coatings prepared via more conventional dip-coating techniques display similar local ordering.

In addition to coatings prepared with the nanoparticle sols, in some embodiments (see, e.g., EXAMPLE 15, infra), sols can be used for facile infiltration of porous materials and subsequent nanocasting of aggregated particulate structures. Examples include infiltration of three-dimensionally ordered macroporous solids, termed 3DOM (i.e., carbon replicas of poly(methyl methacrylate) monoliths [see, e.g., Holland, B. T., et al., (1999) Chem. Mater. 11, 795-805, Blanford, C. F., et al., (1999) Mater. Res. Soc. Symp. Proc. 549, 61-66, Yan, H., et al., (1999) Adv. Mater. 11, 1003-1006, Yan, H., et al., (2000) Chem. Mater. 12, 1134-1141, Yan, H., et al., (2000) Chem. Commun. 1477-1478, Yan, H., et al., (2001) Chem. Mater. 13, 4314-4321, Melde, B. J., et al., (2002) Chem. Mater. 14, 3326-3331, Wang, Z., et al., (2005) Chem. Mater. 17, 6805-6813]) and poly(methyl methacrylate) colloidal crystals for nanocasting of aggregated particulate structures.

The surprising structural stability of the nanoparticles prepared via the methods disclosed herein (see, e.g., EXAMPLES 3-6, infra) is underscored by the retention of their particulate nature in the dried state (i.e., ex situ nanoparticle crystals (see, e.g., EXAMPLE 11, infra), films (see, e.g., EXAMPLES 13-14, infra), and nanocast materials (see, e.g., EXAMPLE 15, infra). Accordingly, in certain embodiments, nanoparticles can be isolated and redispersed in other solvents as an additional means for controlling particle interactions to facilitate longer-range ordering in the synthesized films.

Generally, isolation and dispersion of nanoparticles in pure water and other solvents without induction of particle aggregation (especially for nanoparticles on the order of 10 nm or less) has remained an elusive task. However, in certain embodiments (see, e.g., EXAMPLE 16, infra), dialysis of, e.g., lysine-silica nanoparticle sols against purified water can result in dispersed (i.e., non-aggregated) silica nanoparticles of the same size as those prior to dialysis (i.e., confirmed by SAXS) in pure water. In the case of the simple system disclosed herein, such dialysis cleans free lysine from solution, resulting in sols consisting only of silica nanoparticles in water with lysine present only through possible occlusion in or association with the nanoparticles.

In some embodiments (see, e.g., EXAMPLE 17, infra), the long-term stability of dialyzed sols varies according to conditions employed for TEOS hydrolysis and nanoparticle ageing. Namely, the formation of loose, clear gels has been observed to occur on the time scale of 10 days for dialyzed sols hydrolyzed at room temperature like those described in EXAMPLES 3 and 4. Clear, loose gel formation can occur at longer time scales for dialyzed sols synthesized at elevated temperature (e.g., 60° C.), the synthesis of which is described, for example, in EXAMPLE 5, infra. Silica nanoparticles synthesized at elevated temperatures and subsequently hydrothermally aged (see, e.g., EXAMPLE 6, infra) can remain stable for time scales exceeding months after dialysis.

In some embodiments, rapid room temperature synthesis of well-formed (rather than loose) clear silica gels (see, e.g., EXAMPLE 18, infra) directly from the lysine-silica sols is possible in lieu of the longer-term ageing of dialyzed sols described, for example, in EXAMPLE 17, infra. Gelation can be induced through titration of the as-synthesized sols with compatible peptide oligomers having appropriate pKa's (e.g., di-lysine). This titration effectively reduces the pH of the lysine-silica sol, and leads to the eventual formation of optically clear gels. In certain embodiments (see, e.g., EXAMPLE 19, infra), the morphology (e.g., monoliths, interconnected plates) and porosity (e.g., from non-porous to micro- and mesoporosity) of the clear gels can be effectively tuned by modulation of silica content of the original sols (as described, for example, in EXAMPLE 4, infra). The amount of the peptide oligomer required to induce gelation generally decreases with increasing silica content.

For example, peptide oligomer content, specifically di-lysine, can be in a range from 0 mM to 9 mM (e.g., from 1 mM to 5 mM, from 5 mM to 7 mM, from 7 mM to 8 mM, from 8 mM to 9 mM) In some embodiments, di-lysine content can be about 1 mM or more (e.g., about 3 mM or more, about 5 mM or more, about 8 mM or more). In certain embodiments, di-lysine content can be about 9 mM or less (e.g., about 8 mM or less, about 7 mM or less, about 6 mM or less). It is believed that increasing di-lysine content can lead to gel formation.

In certain embodiments (see, e.g., EXAMPLE 20, infra), the final density of the hydrogel can be modulated by dilution of the sol prior to titration with the peptide oligomer. EXAMPLE 20 describes a 50:50 volumetric dilution of a high-silica sol with a buffer solution prior to titration with the compatible peptide-oligomer di-lysine.

In some embodiments, silica gels can be of a physiological nature and have tunable micro- and mesoporosity (see, e.g., EXAMPLE 21, infra). Namely, the tunable porosity and physiological nature of the silica nanoparticle gel can provide a suitable environment for either immobilization or three-dimensional encapsulation of living cells [see, e.g., Baca, H. K. et al., (2006) Science. 313, 337-341] with applications, for example, in the areas of in vivo therapeutics and drug delivery. Encapsulation and persistent viability of human umbilical vein endothelial cells (HUVECs) and INS-1 insulinoma cells with the gels resulting from the lysine-silica sols, is described, for example, in EXAMPLE 21, infra. The associated porosity of the gels formed from the nanoparticle sols disclosed in this invention deems them as good scaffolds for supporting and/or sustaining cell viability, protecting them from immunological attack during implantation, and regulating nutrient uptake and metabolite release.

In some embodiments (see, e.g., EXAMPLE 22, infra), two-dimensional (e.g., surface) support of living cells on silica nanoparticle films is possible. For example, films described in EXAMPLES 13-14, infra, have been employed to confirm the limited cell adhesion on silica nanoparticle films, a phenomenon described in [Cousins, B. G., et al., (2004) Journal of Materials Science: Materials in Medicine. 15, 355-359]. In the example described in EXAMPLE 22 a facile means is discussed for capitalizing on this selective cell adhesion for periodic cell patterning using the banded silica nanoparticle films of EXAMPLE 14.

EXAMPLES

Example 1

TEOS Hydrolysis in Pure Water in the Absence of Additional Hydrolytic Agents

Figure 2:
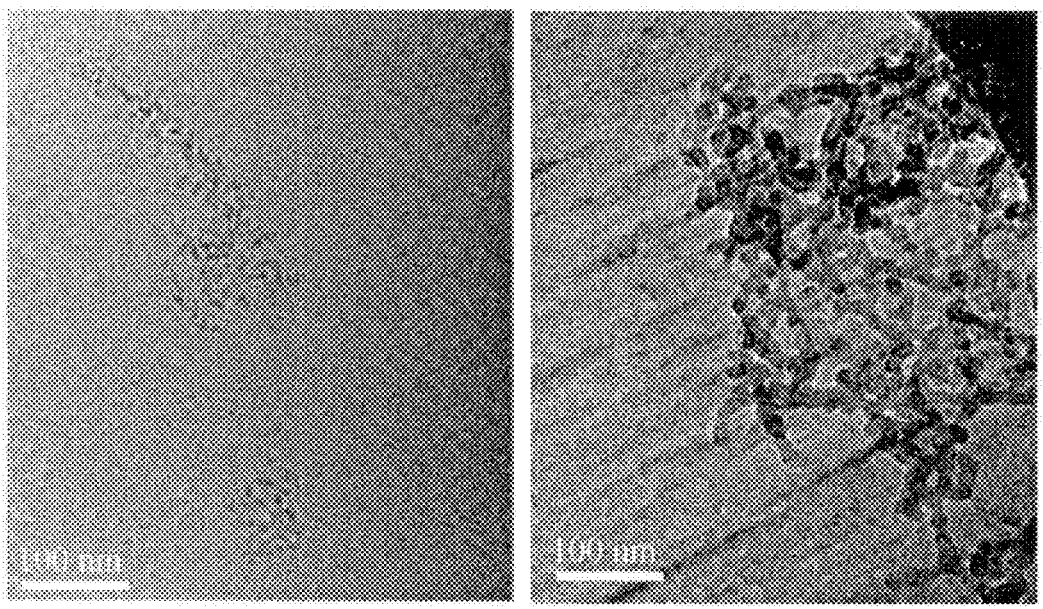
FIG. 2 shows cryo-TEM images of two representative regions of a vitrified sol prepared through hydrolysis of tetraethylorthosilicate (TEOS, 98% Aldrich) in distilled water with no additional hydrolytic agents. Images are at the same magnification to highlight the particle size dispersity.

A polydisperse population of silica nanoparticles was prepared through hydrolysis of tetraethylorthosilicate (TEOS, 98% Aldrich) in distilled water with no additional hydrolytic agents. The clear sol of silica nanoparticles having a molar composition of 20 $SiO_2$:9500$H_2O$:80 ethanol was prepared by adding the prescribed amount of TEOS to distilled water and vigorously stirring. Complete hydrolysis was denoted by the production of a clear sol after approximately 48 hours of mixing. FIG. 1 shows small angle x-ray scattering patterns collected from the resulting sol, characteristic of a wide range of nanoparticle sizes. Representative cryogenic transmission electron microscopy (cryo-TEM) images of the same sol are shown in FIG. 2, and depict a polydisperse population of nanoparticles. The majority of the particles in this sol formed aggregates like those shown in the cryo-TEM images of FIG. 2.

Example 2

Clear Gel Formation Through Ageing of Silica Nanoparticle Sols in Pure Water

The nanoparticle sol of EXAMPLE 2 was aged for 1-3 days during which the clear sol transformed into a clear, well-formed gel. Cryo-TEM images in FIG. 2 show the aggregation of nanoparticles into clusters, characteristic of the early stages of gelation.

Example 3

Figure 3:
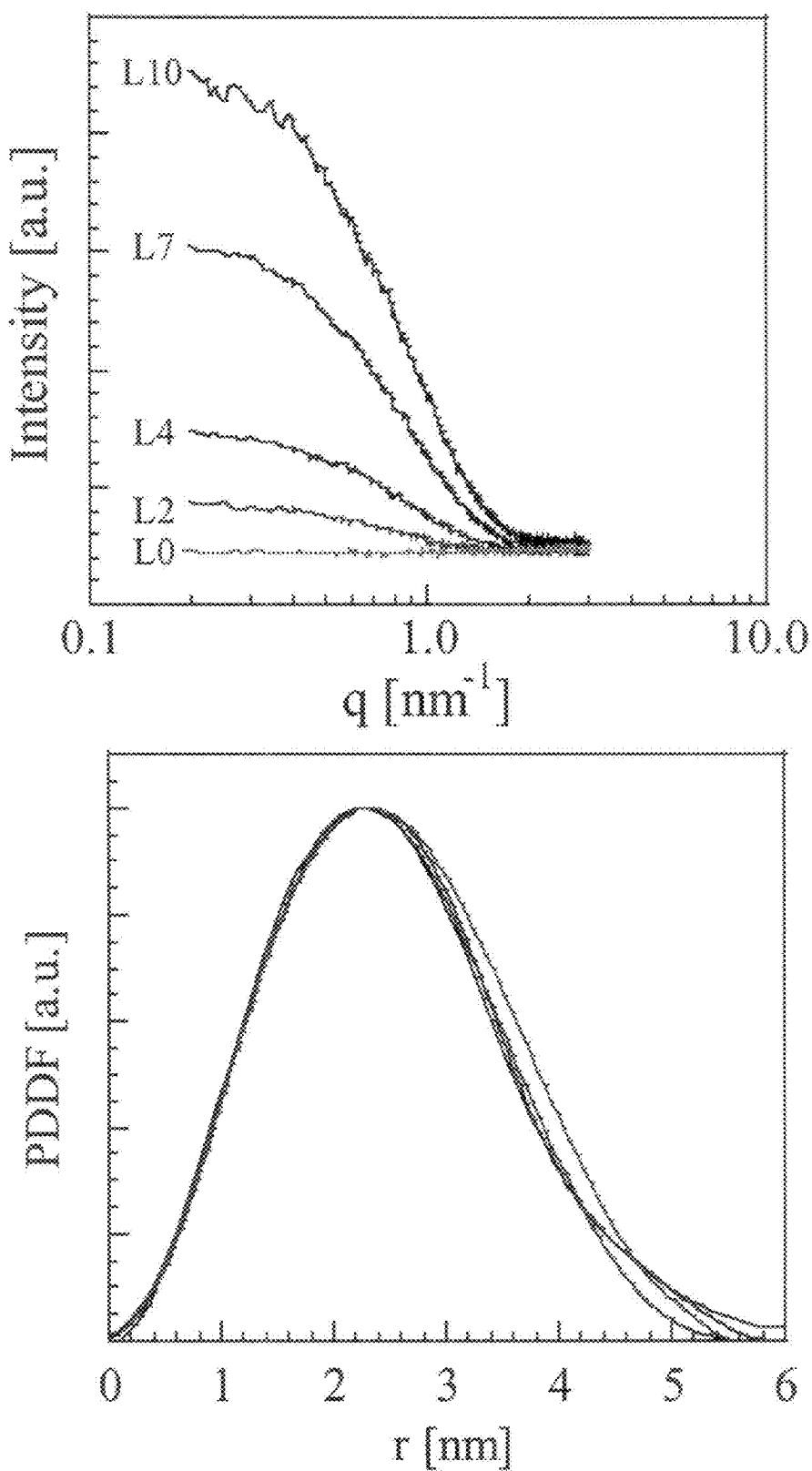
FIG. 3 shows (top) small angle x-ray scattering curves for lysine-silica solutions L0 through L10, having respective molar compositions of x $SiO_2$ 5.8 lysine:9500 water:4x ethanol, where x=0, 1.75, 3.5, 7, 10. The scattering profiles show increasing intensity with increasing silica content. PDDF (bottom) show that the average particle radius (c.a. 2.3 nm) is approximately constant for this range of silica concentrations.
Figure 4:
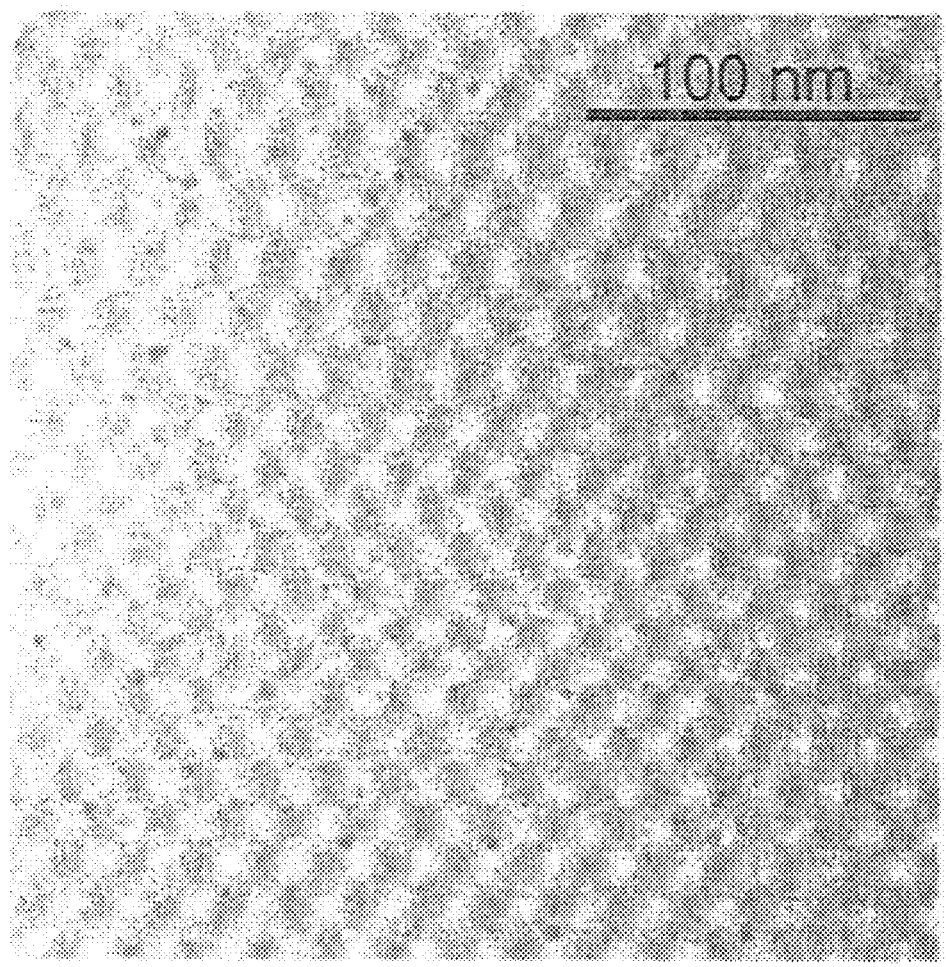
FIG. 4 shows a cryo-TEM image of the a sol of molar composition 3.5 $SiO_2$:5.8 lysine:9500 water:14 ethanol depicting nanoparticles of approximately 4.5 nm in diameter.

Synthesis of Silica Nanoparticles Through TEOS Hydrolysis in Lysine-Silica Sols at Room Temperature Silica nanoparticles were prepared at room temperature in un-buffered, optically clear aqueous solution of L-lysine (Sigma-Aldrich), tetraethylorthosilicate (TEOS, 98% Aldrich), and distilled water with molar composition of x $SiO_2$: 5.8 Lysine:9500$H_2O$ 4x Ethanol ranging from x=0 to 10 (denoted accordingly as L0, L2, L4, L7, and L10 in FIG. 3). Clear sols were prepared by first mixing lysine with distilled water. Subsequent addition of the prescribed amounts of TEOS, carried out under vigorous stirring for at least 24 hours, ensured complete hydrolysis. Cryo-TEM images of the resulting sols (FIG. 4) revealed spherical nanoparticles in solution. SAXS patterns (FIG. 3) collected for the sols at room temperature (25° C.) with a SAXSess instrument employing Cu—K$_\alpha$ radiation revealed increasing intensity with increasing silica content. PDDF analysis of the SAXS patterns (FIG. 3) pointed to a relatively constant average particle radius for the investigated sols of approximately 2.3 nm. This implied that the increasing intensity observed during SAXS analysis resulted from increasing nanoparticle concentration with increasing silica concentration.

Example 4

Tuning of Silica Nanoparticle Size Through Total Silica Content

Figure 5:
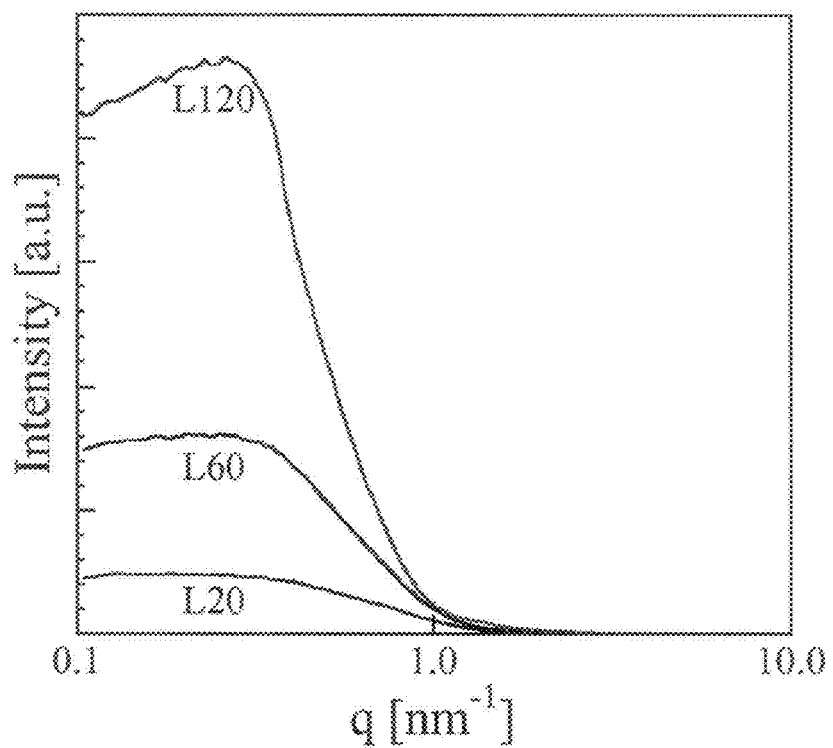
FIG. 5 shows small angle x-ray scattering patterns for lysine-silica sols L20, L60, and L120, having respective molar compositions of x $SiO_2$:5.8 lysine:9500 water:4x ethanol, where x=20, 60, and 120.
Figure 6:
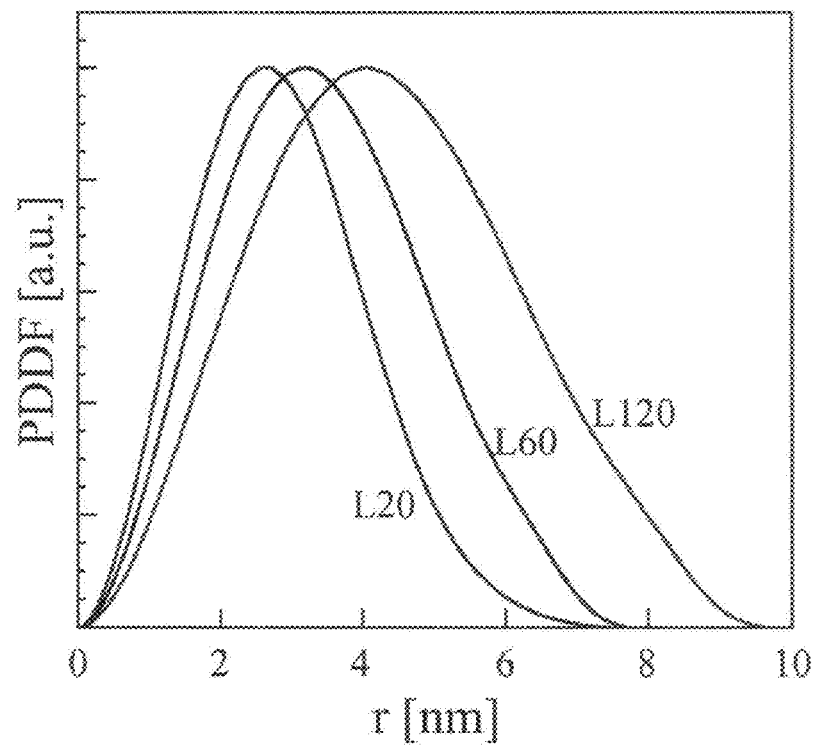
FIG. 6 shows PDDF for the sols of FIG. 5 indicating that the average particle radius increases with increasing silica content from approximately 2.6 nm (L20) to 3.2 nm (L60) to 4.0 (L120).

The sols described in EXAMPLE 3 were prepared with higher silica content to yield sols with molar composition of x SiO$_2$:5.8 lysine:9500 Water:4x Ethanol, where x ranged from 10 to as large as 500. A representative series of SAXS patterns and extracted PDDFs are shown in FIGS. 5 and 6, respectively, for increasing molar silica composition of x=20, 60, 120. The shift of the scattering to higher q and the PDDF to larger radius with increasing silica content underscores the sensitivity of the nanoparticle size to increasing silica content well above the silica solubility limit (i.e., the compositions explored in EXAMPLE 3).

Example 5

Figure 7:
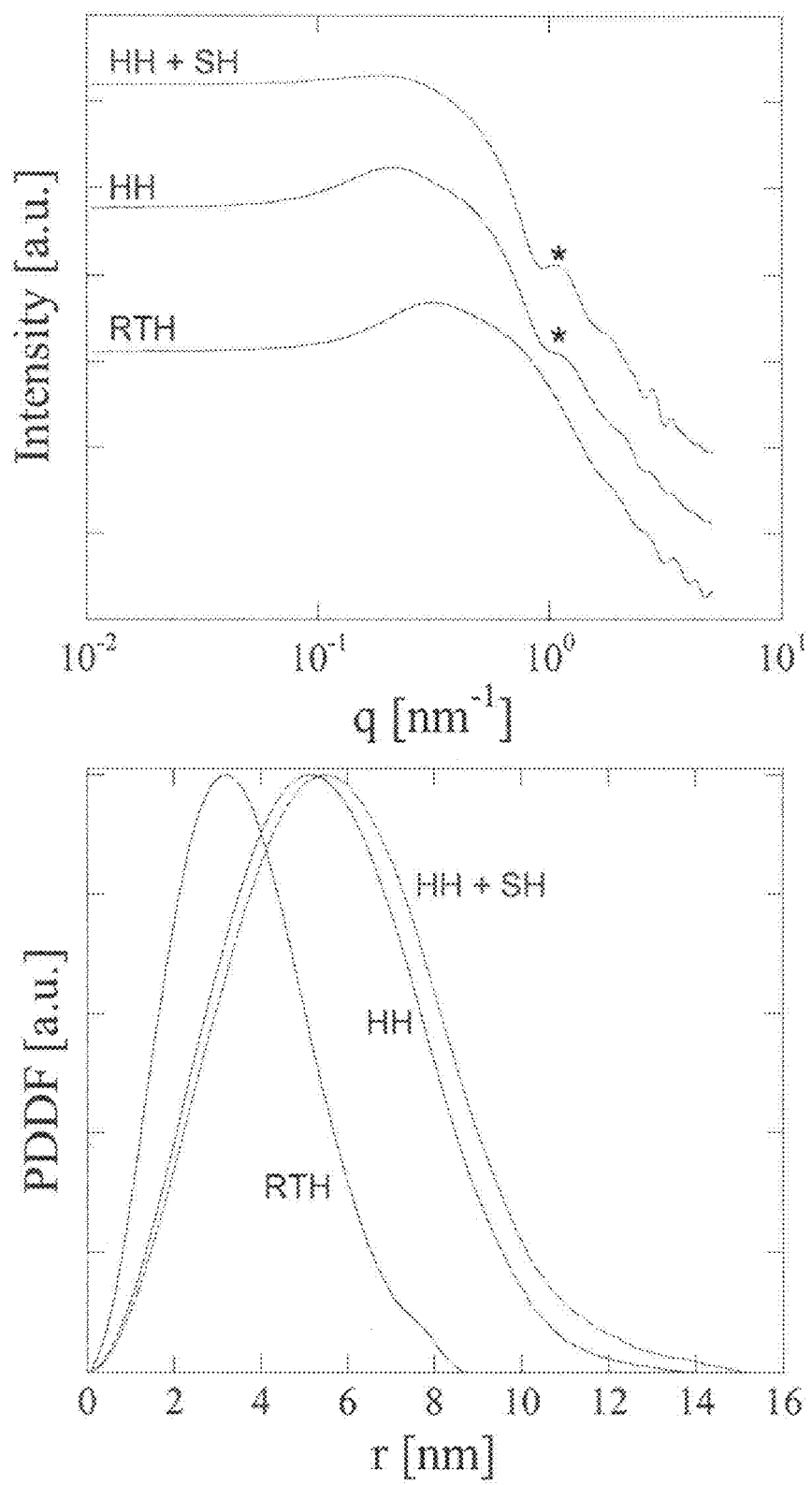
FIG. 7 shows (top) desmeared small angle x-ray scattering patterns for lysine-silica sols of molar composition 60 $SiO_2$:5.8 lysine:9500 water:240 ethanol hydrolyzed at room temperature (RTH), at 60° C. (HH), and at 60° C. followed by 20 hours of hydrothermal ageing at 100° C. (HH+SH). The '*' marks the higher-order maxima in the scattering patterns, indicative of a high degree of monodispersity. PDDF (bottom) provide insight into the corresponding nanoparticle size.
Figure 8:
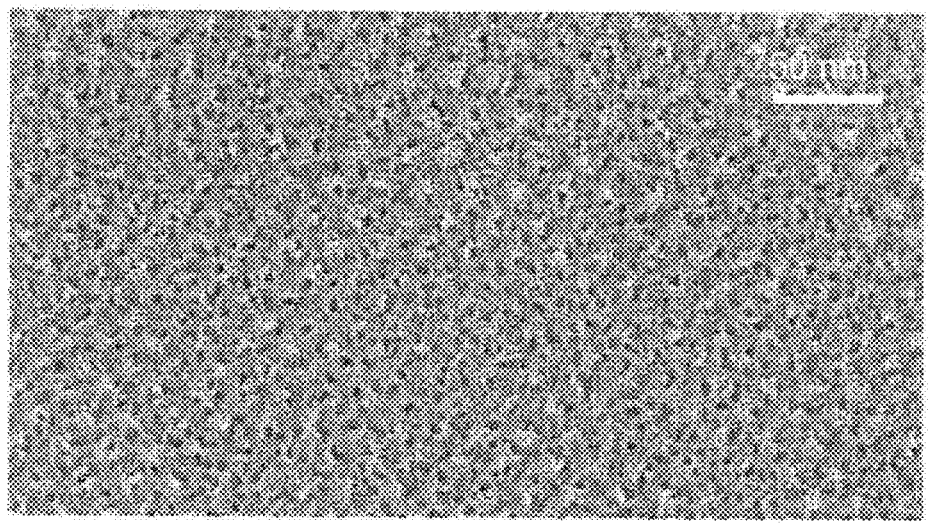
FIG. 8 shows cryo-TEM images of the nanoparticle sols characterized in FIG. 7 indicating the change in size and morphology with synthesis conditions.
Figure 8:
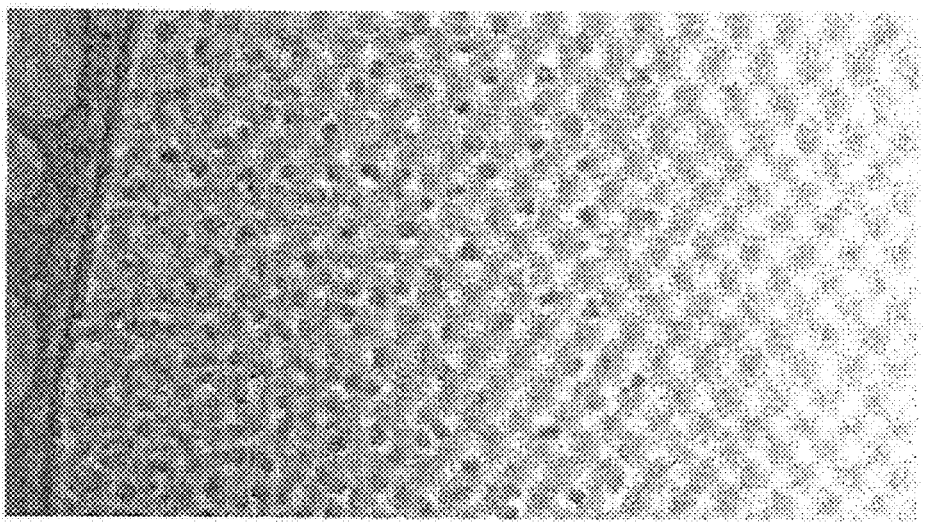
Figure 8:
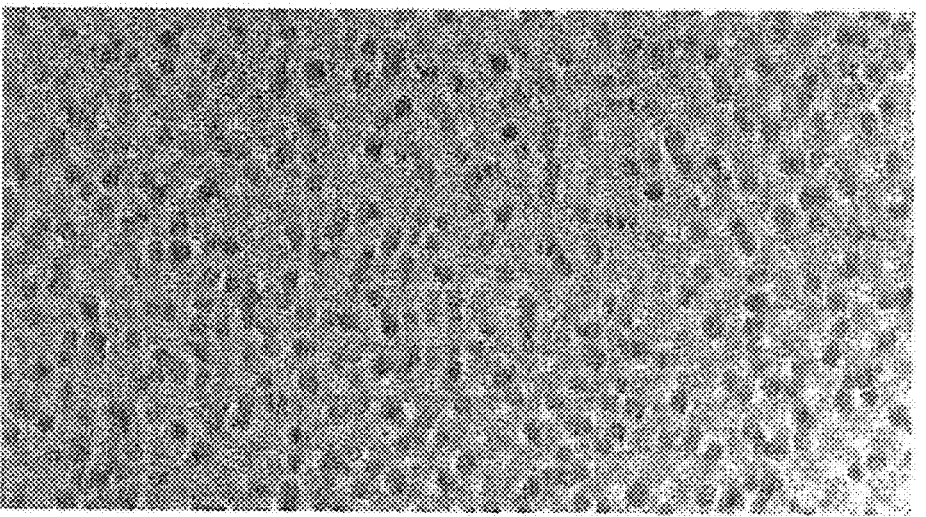

Synthesis of Silica Nanoparticles Through TEOS Hydrolysis in Lysine-Silica Sols at Elevated Temperatures The sols described in EXAMPLE 3 and 4 were hydrolyzed at elevated temperatures up to 60° C. Clear sols were prepared by first mixing lysine with distilled water and heating the mixture for at least 30 minutes at the prescribed temperature. The prescribed amount of TEOS was then added, and the mixture was vigorously stirred for at least 20 hours to ensure complete hydrolysis. FIG. 7 shows comparative SAXS patterns and the extracted pair distance distribution function (PDDF) for a series of representative sols of the same molar composition (60 SiO$_2$:5.8 lysine:9500 Water:240 Ethanol). Comparisons can be drawn between the sol hydrolyzed at 60° C. (denoted as HH) and the sol prepared as in EXAMPLE 4 by hydrolysis at room temperature (denoted RTH). The comparative shift of the maxima of the scattering pattern to lower q and the PDDF to larger radius points to a marked increase in particle size with increase in hydrolysis temperature. Cryo-TEM images of the nanoparticle sols (labeled RTH and HH) are shown in FIG. 8, confirming the increase in particle size with heating.

Example 6

Synthesis of Silica Nanoparticles Through TEOS Hydrolysis in Lysine-Silica Sols at Elevated Temperatures Followed by High-Temperature Ageing Following complete hydrolysis of the samples described in EXAMPLE 5, the sols were transferred to teflon lined stainless steal autoclaves and were heated without stirring or rotation at temperatures up to 100° C. FIG. 7 shows SAXS patterns and the extracted pair distance distribution function (PDDF) for a sol of molar composition 60 SiO$_2$:5.8 lysine: 9500 Water:240 Ethanol for which hydrolysis was carried out at 60° C., and was followed by static heating (denoted HH+SH) in comparison to samples described in EXAMPLES 3-5. The slight shift of the maxima of the scattering pattern to lower q and the PDDF to larger radius points to a slight increase in particle size with increase in ageing temperature. The increase in size from the sol synthesized as in EXAMPLE 5 at 60° C. (HH) is more subtle than observed between that sample and the one synthesized at room temperature (EXAMPLE 3, RTH). Instead, as shown by the cryo-TEM image in FIG. 8, an apparent perfection of the particles to a more spherical shape occurs upon heating.

Example 7

Quantification of Silica Nanoparticle Monodispersity

Figure 9:
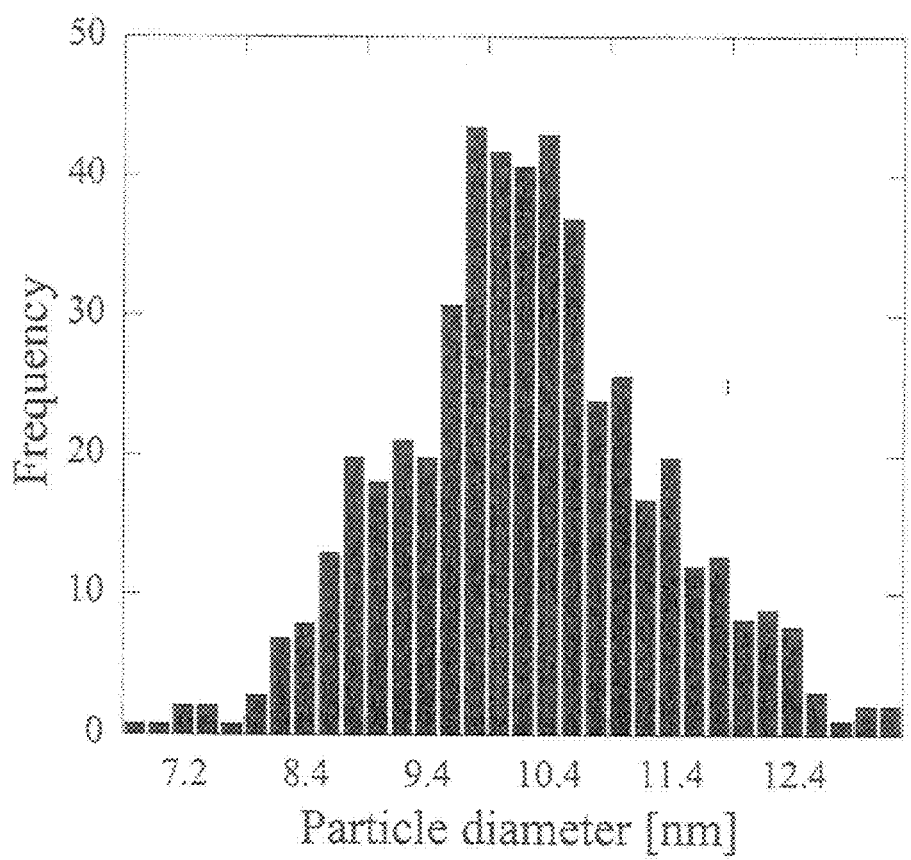
FIG. 9 shows (top) the particle size distribution for a sol of molar composition 60 $SiO_2$:5.8 lysine:9500 water:240 ethanol hydrolyzed at 60° C. and hydrothermally aged at 100° C. Particle sizes were extracted directly from the cryo-TEM image (bottom) of the same sol.
Figure 9:
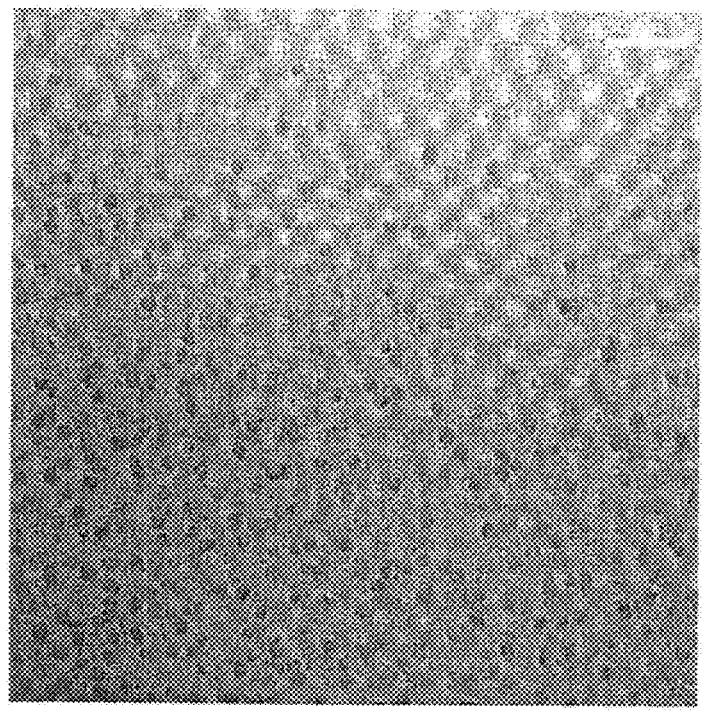

Representative silica nanoparticles of EXAMPLES 3-6 were measured directly from cryo-TEM images of the particles (500 particles measured for statics). An example particle size distribution and corresponding cryo-TEM image of the representative sols from EXAMPLE 6 are shown in FIG. 9. The particle size distribution reveals a highly monodisperse population of particles of size 10±1.1 nm with a standard deviation in particle size of only 11%. The magnitude of the measured diameter is in good agreement with SAXS estimates (Particle diameter~10.5-11 nm based upon the maximum of the PDDF) for the same sol in EXAMPLE 6 for the nanoparticles synthesized via TEOS hydrolysis followed by hydrothermal ageing at 100° C.

Example 8

Tuning of Silica Nanoparticle Size Via Stir Rate During TEOS Hydrolysis

Figure 10:
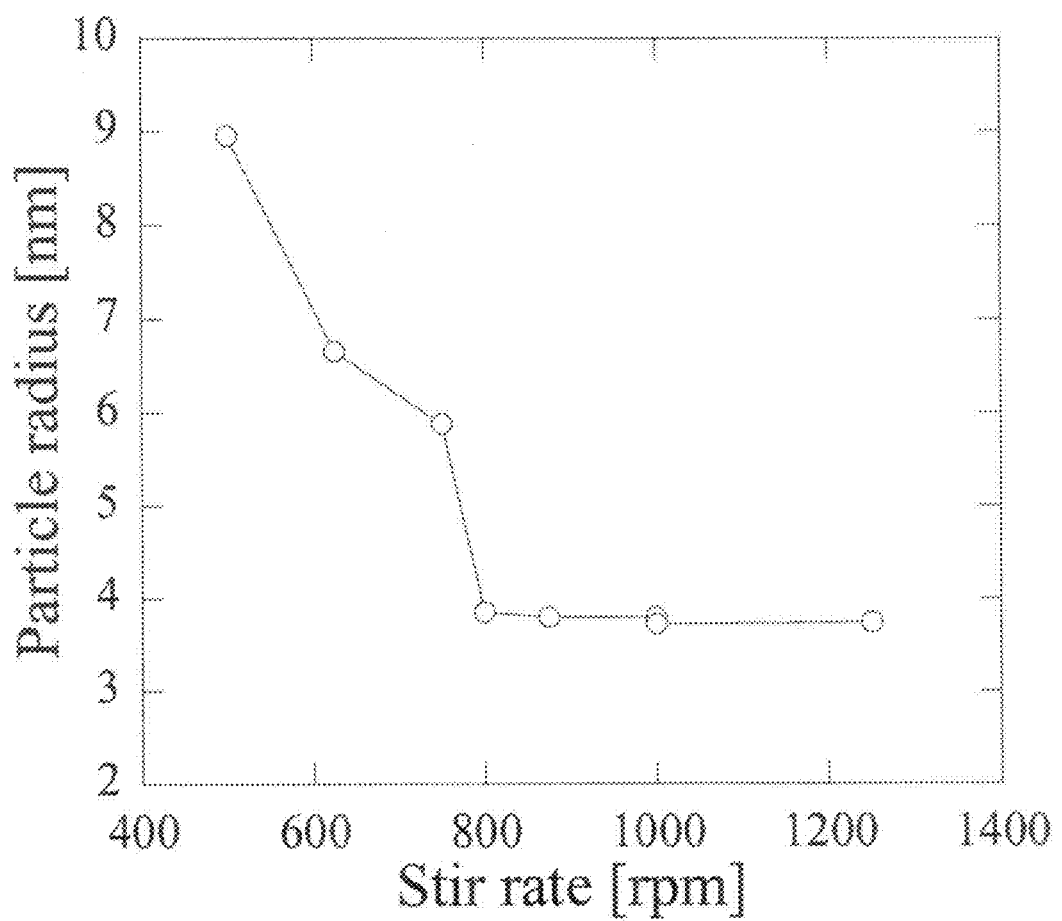
FIG. 10 shows the sensitivity of particle size to rate of sol homogenization during hydrolysis for a representative sol of molar composition 60 $SiO_2$:5.8 lysine:9500 water:240 ethanol hydrolyzed at 60° C.

The sols described in EXAMPLES 5-6 were prepared with hydrolysis carried out at varied stirring rates, ranging from as small as 500 rpm to as large as approximately 1200 rpm. FIG. 10 shows the effect of stirring rate (i.e., sol homogenization) during hydrolysis on the final particle size for a representative sol of molar compositions 20 SiO$_2$:5.8 lysine:9500 Water:80 Ethanol. Surprisingly, particle size is apparently a strong function of sol homogenization especially for slower stir rates. Namely, particle size at slow stir rates can be more than 200% larger than particle sizes when hydrolysis is carried out with vigorous stirring.

Example 9

Figure 11:
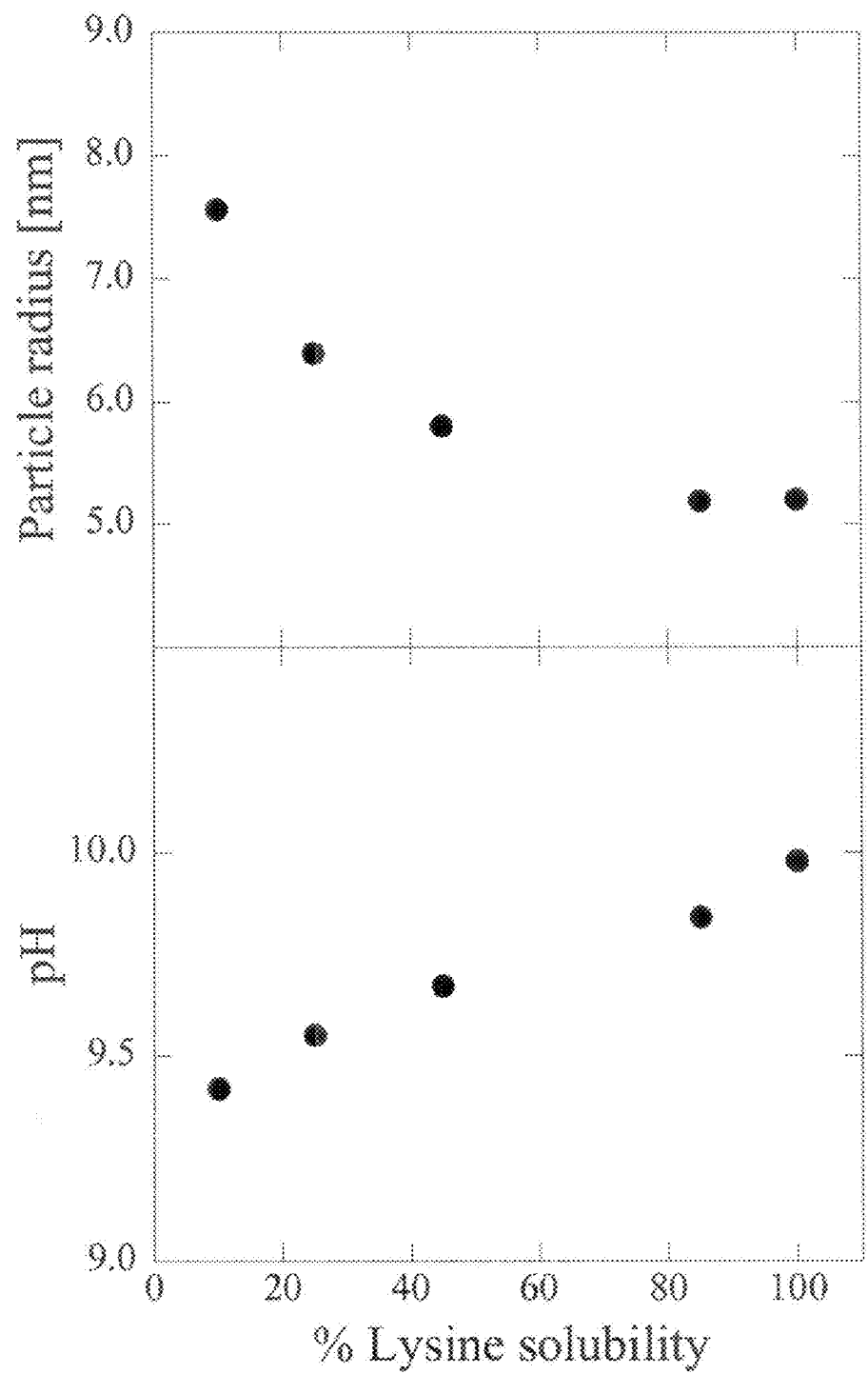
FIG. 11 shows (top) the sensitivity of particle size to the lysine concentration in the sol (reported as the percent of the lysine solubility limit in water) and (bottom) the corresponding changes in pH. The representative data is from a sol of molar composition 60 $SiO_2$:5.8 lysine:9500 water:240 ethanol hydrolyzed at 60° C.

Tuning of Silica Nanoparticle Size Through pH Modification Via Adjustment of Lysine Content The sols of EXAMPLES 3-6 were prepared with varied molar lysine compositions of y lysine:9500 Water, spanning from y=0 to 6.9, where the latter corresponds to 100% of the lysine solubility limit in water. Varying lysine content directly affects the pH of the sol due to its dependence on lysine speciation. FIG. 11 shows resulting trends in particle size (i.e., estimated from the maximum of PDDF extracted from each SAXS patterns measured from the sols) with increasing lysine content for different lysine compositions and the concomitant change in pH. Representative data for a sol of EXAMPLE 5 of molar composition 60 SiO$_2$:y lysine:9500 Water:240 Ethanol are shown. Generally, particle size increases with decreasing sol pH, induced by decreasing lysine content.

Example 10

Figure 12:
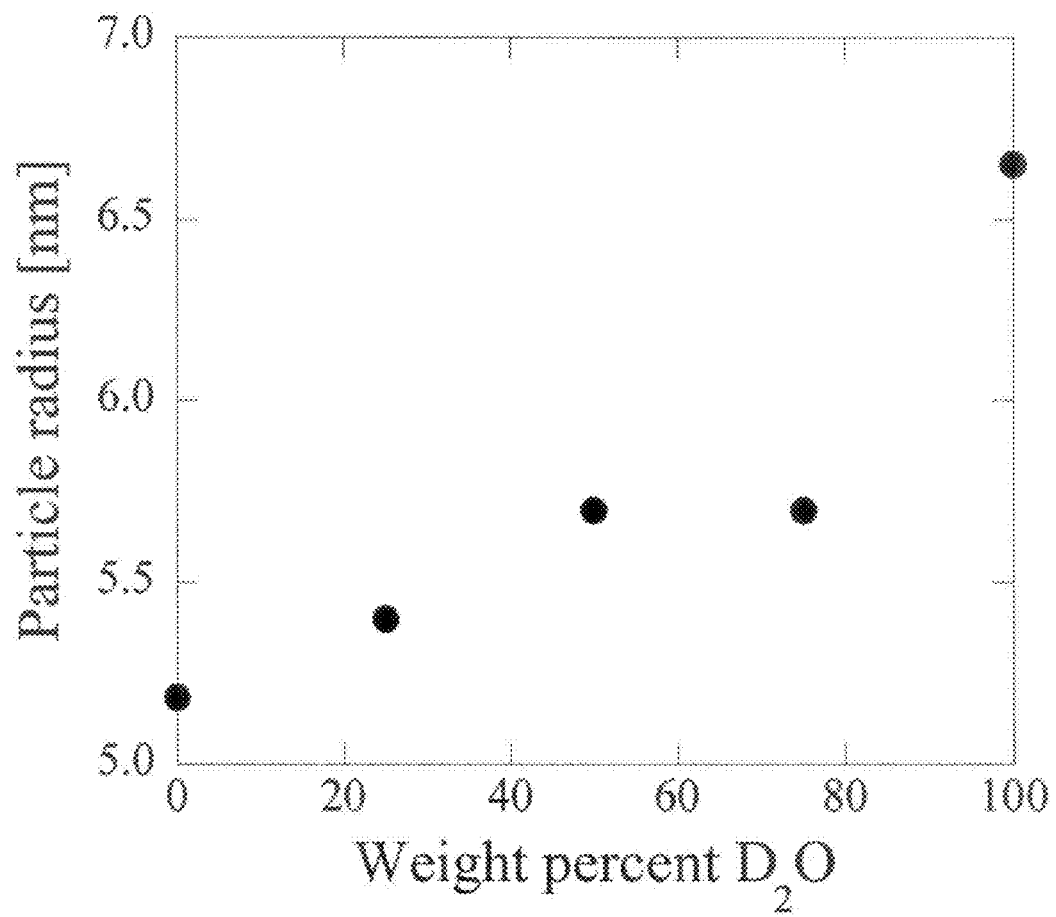
FIG. 12 shows the sensitivity of silica nanoparticle size to the fractional deuteration of the aqueous nanoparticle sol for a sol of molar composition 60 $SiO_2$:5.8 lysine:9500 water:240 ethanol hydrolyzed at 60° C.

Tuning of Silica Nanoparticle Size Via Deuterium Oxide Fraction of Hydrolysis Mixtures Sols were prepared identically to those described in EXAMPLES 3-6 except with molar substitution of water with deuterium oxide to yield sol compositions of x SiO$_2$:y lysine:z D$_2$O:9500-z Water:4x Ethanol, where silica compositions ranged from x=20 to 60 and lysine compositions ranged from y=1.7 to 5.8. FIG. 12 depicts the sensitivity of silica nanoparticle size to increasing molar substitution of deuterium oxide for water for a sol of EXAMPLE 5. The particle size, extracted from PDDF analysis of SAXS patterns of the nanoparticle sols, increases with increasing deuteration of the aqueous solvent.

Example 11

Ex Situ Assembly of Nanoparticle Crystals Through Room Temperature Evaporation

Figure 13:
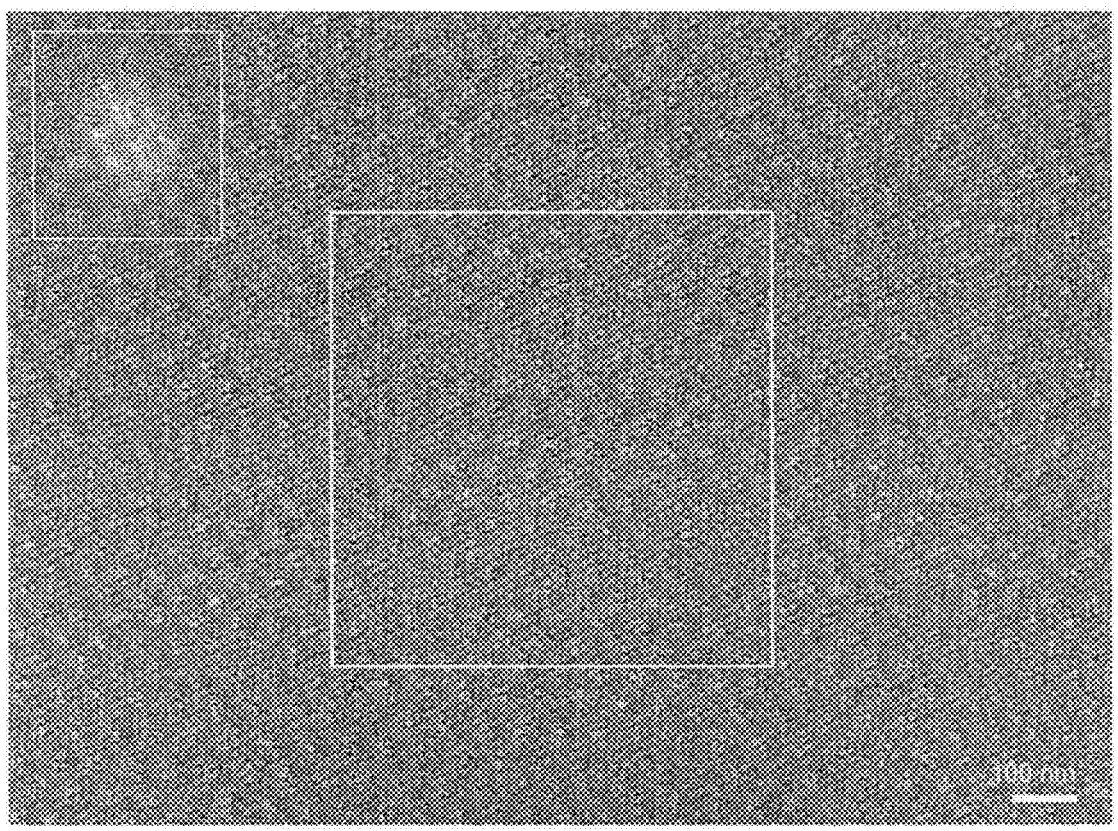
FIG. 13 shows an SEM image of a lysine-silica sol (molar composition 60 $SiO_2$:5.8 lysine:2850 $D_2O$:6650 Water:240 Ethanol) after evaporative drying. The inset shows a Fourier transform pattern computed from the highlighted region (square outline).

The nanoparticle sols of EXAMPLES 5, 6, and 9 were dried by room temperature evaporation on carbon tape for subsequent SEM imaging. Drying of the sols resulted in the formation of large ordered nanoparticle crystals extending beyond scales of 10 μm. FIG. 13 shows a top view of a representative nanoparticle crystal synthesized by evaporative drying of a sol of molar composition 60 $SiO_2$:5.8 lysine: 2850 $D_2O$:6650 Water:240 Ethanol. The inset shows a Fourier transform pattern computed from the highlighted region (square outline) confirming the long-range nanoparticle ordering.

Example 12

In Situ Assembly of Nanoparticle Crystals Near Fixed Boundaries

Figure 14:
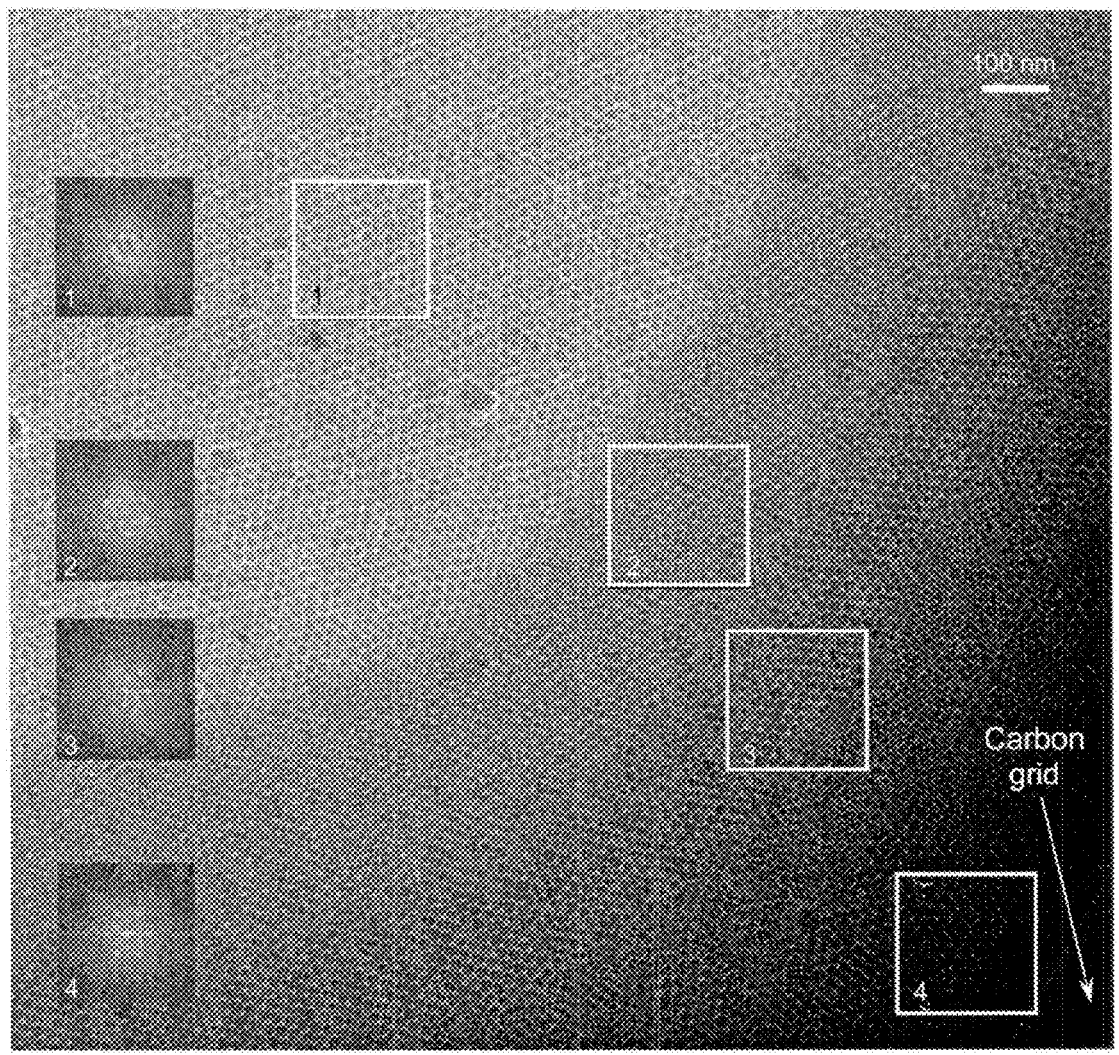
FIG. 14 shows a cryo-TEM image of ordered nanoparticles in a vitrified lysine-silica sol (60 $SiO_2$:5.8 lysine:2850 $D_2O$:6650 Water:240 Ethanol; 1% v nanoparticles) in the vicinity of a carbon TEM grid. Progressively darker bands of nanoparticles observed in moving towards the carbon skeleton correspond to the development of close-packed multilayers with increasing sample thickness. Fourier transforms of regions (white boxes) within each band are shown as insets on the left.

The nanoparticle sols of EXAMPLES 5, 6 and 9 were vitrified in holey carbon TEM grids. Cryo-TEM imaging revealed the formation of ordered, multilayer nanoparticle crystals near the rigid skeleton of the carbon grid. FIG. 14 shows a cryo-TEM image of ordered nanoparticles in a vitrified sol of molar composition 60 $SiO_2$:5.8 lysine:2850 $D_2O$: 6650 Water:240 Ethanol; 1% v nanoparticles) in the vicinity of a carbon grid. Progressively darker bands of nanoparticles observed in moving towards the carbon skeleton correspond to the development of close-packed multilayers with increasing sample thickness. Fourier transforms of regions (white boxes) within each band are shown as insets on the left, and confirm the high degree of ordering of the nanoparticles confined through vitrification near a fixed boundary.

Example 13

Figure 15:
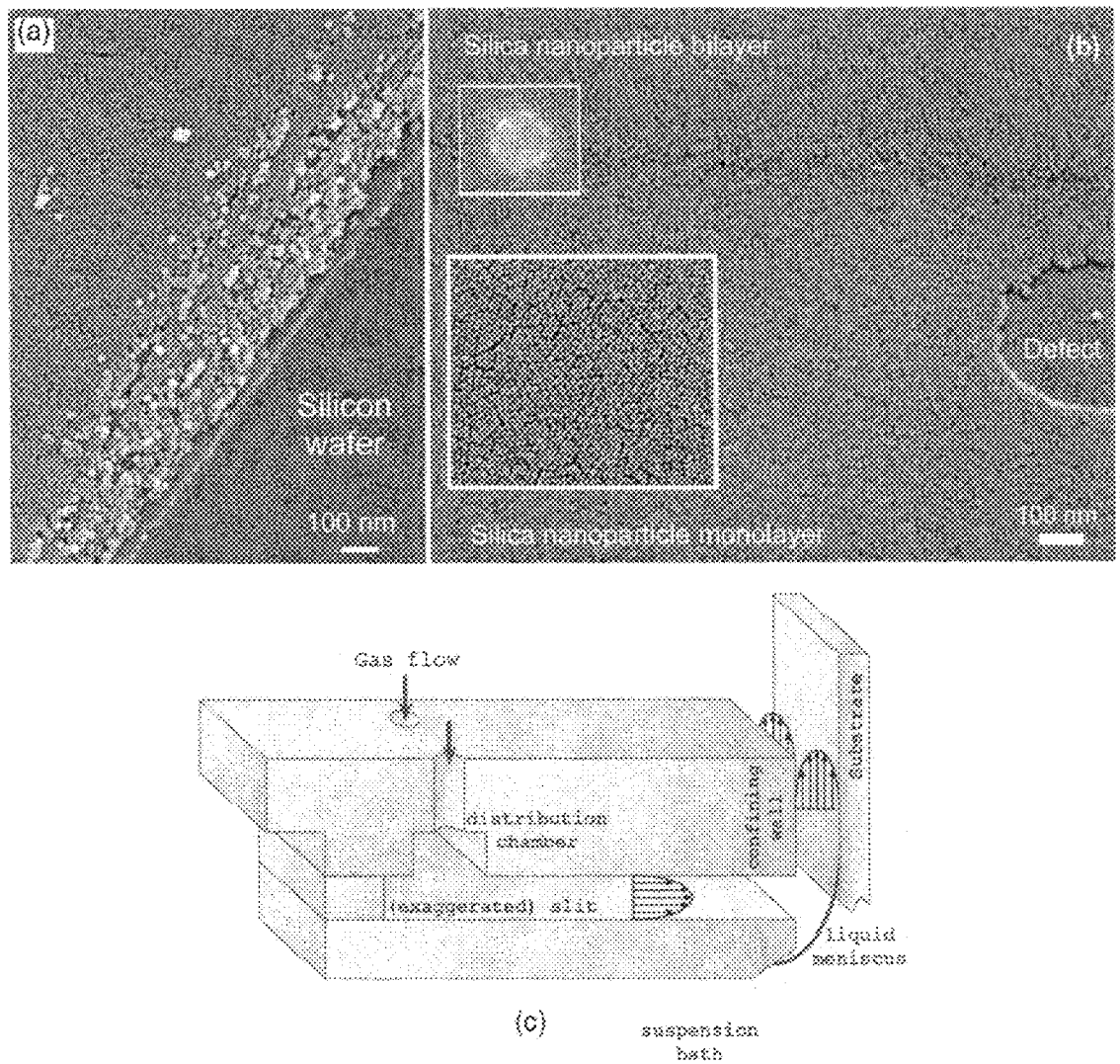
FIG. 15 shows SEM images of nanoparticle films resulting from coating lysine-silica sols of molar composition (a) 60 $SiO_2$:1.7 lysine:9500 Water:240 Ethanol (1% v nanoparticles) and (b) 60 $SiO_2$:1.7 lysine:3.7×10$^5$ Water:240 Ethanol (0.02% v nanoparticles) on a silicon wafer. Dip-coating was carried out using a coating device schematized in (c) at (a) 20 and (b) 6 cm hr$^{-1}$, in each case under a flow of 3 SCFH of $N_2$. Panel (a) shows a cross-section of a multilayer film. In panel (b), the sample has been tilted to emphasize the bilayer-to-monolayer step (step edge marked partially by dashed line). The inset in (b) shows a top-view of the monolayer depicting the local ordering confirmed by the representative Fourier transform pattern.

Multi- and Near Mono-Layer Semi-Ordered Nanoparticle Films by Dip-Coating and Evaporation-Induced Self-Assembly A coating apparatus described in detail in [Snyder, M. A., et al., (2007) Langmuir. 23, 9924-9928] and depicted in FIG. 15c was employed to directly coat nanoparticle sols of EXAMPLES 5-6 onto silicon substrates. Generally, the apparatus withdrew from the static nanoparticle sol a substrate at a controlled rate and under a prescribed flow of dry nitrogen. Draw rate, nitrogen flow rate (i.e., solvent evaporation rate), and sol concentration were all controlled during film deposition. Nitrogen flow rates ranging from 1 to 3 SCFM, and substrate withdraw rates ranging from 1 to 6 cm $hr^{-1}$ were investigated. FIG. 15a shows an SEM image of a multilayer film of silica nanoparticles coated from a sol of molar composition 60 $SiO_2$:1.7 lysine:9500 Water:240 Ethanol (1% v nanoparticles) on a silicon wafer at a rate of 20 $cm^{-1}$ and under a flow of 3 SCFH of $N_2$. Tuning of film thickness was possible by changing coating rates. Namely, FIG. 15b shows and SEM image of a near-monolayer film resulting from coating a sol of molar composition 60 $SiO_2$:1.7 lysine:3.7× $10^5$ Water:240 Ethanol (0.02% v nanoparticles) on a silicon wafer at 6 cm $hr^{-1}$ under a flow of 3 SCFH of $N_2$. The bottom inset shows a plan-view of the film surface, and the Fourier transform pattern shown in the top inset confirms local ordering of the films. Similar coatings were also made on glass coverslips by externally fixing submerged coverslips in a sol reservoir and subsequently lowering the reservoir at a controlled rate. This suggests that realization of such coatings is independent of the specific coating apparatus, and that different substrates can be employed.

Example 14

Figure 16:
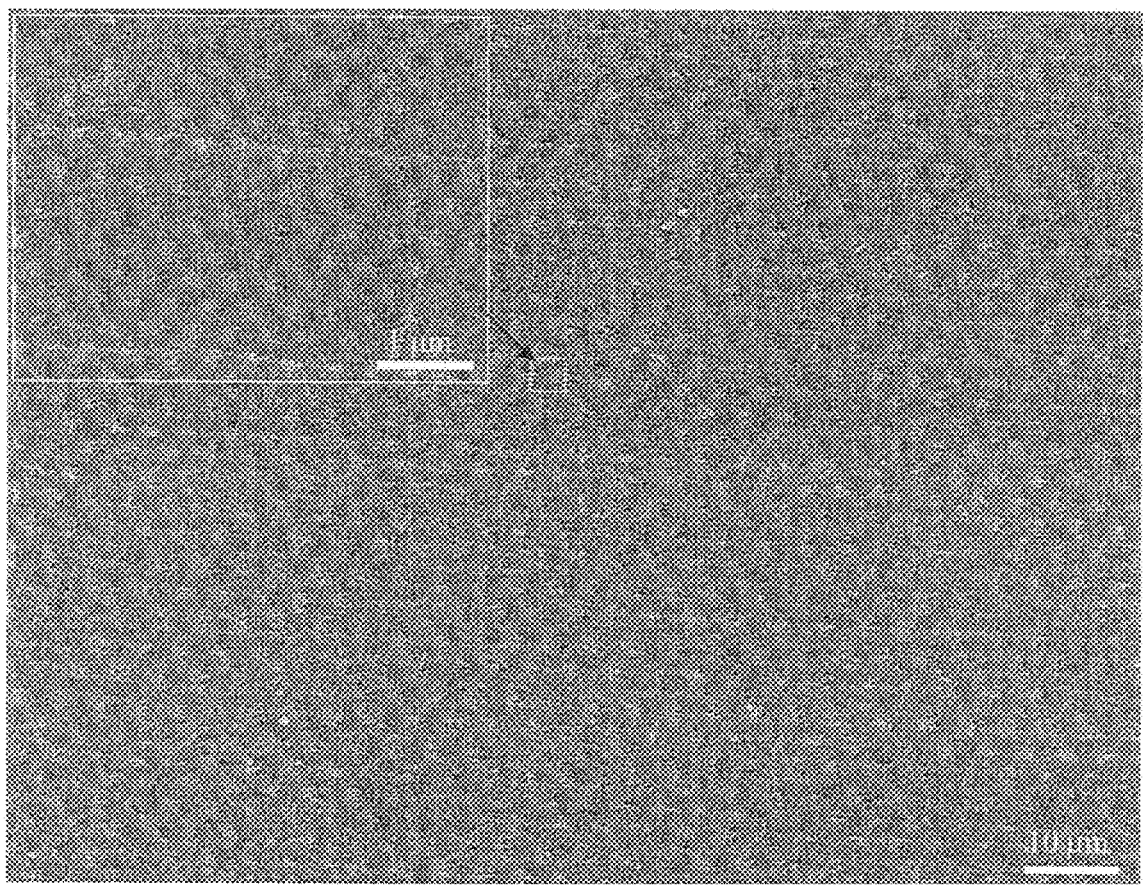
FIG. 16 shows an SEM image of a silica nanoparticle coating using a sol of molar composition $SiO_2$:1.7 lysine:3.7× 10$^5$ Water:240 Ethanol (0.02% v nanoparticles), coated at a rate of 20 cm hr$^1$ and under a nitrogen flow rate of 3 SCFH. The result is a periodic film with alternating bands of silica nanoparticles and bare substrate, highlighted in the inset.

Coating of Semi-Periodic Banded Nanoparticle Structures by Dip-Coating and Evaporation-Induced Self-Assembly Coatings described in EXAMPLE 12 carried out at the higher dipping speeds (i.e., up to 20 cm $hr^{-1}$) lead to semi-periodically discontinuous films, characterized by alternating bands of silica monolayers and bare substrate. Control of the band width and band periodicity was achieved by varying dipping rate and volumetric nitrogen flow rate (i.e., evaporation rate). FIG. 16 shows a representative periodic film prepared by coating a sol of molar composition 60 $SiO_2$:1.7 lysine:3.7×$10^5$ Water:240 Ethanol (0.02% v nanoparticles) on a silicon wafer at 11 $cm^{-1}$ under a flow of 3 SCFH of $N_2$. The inset shows a higher magnification image of several of the silica nanoparticle bands.

Example 15

Figure 17:
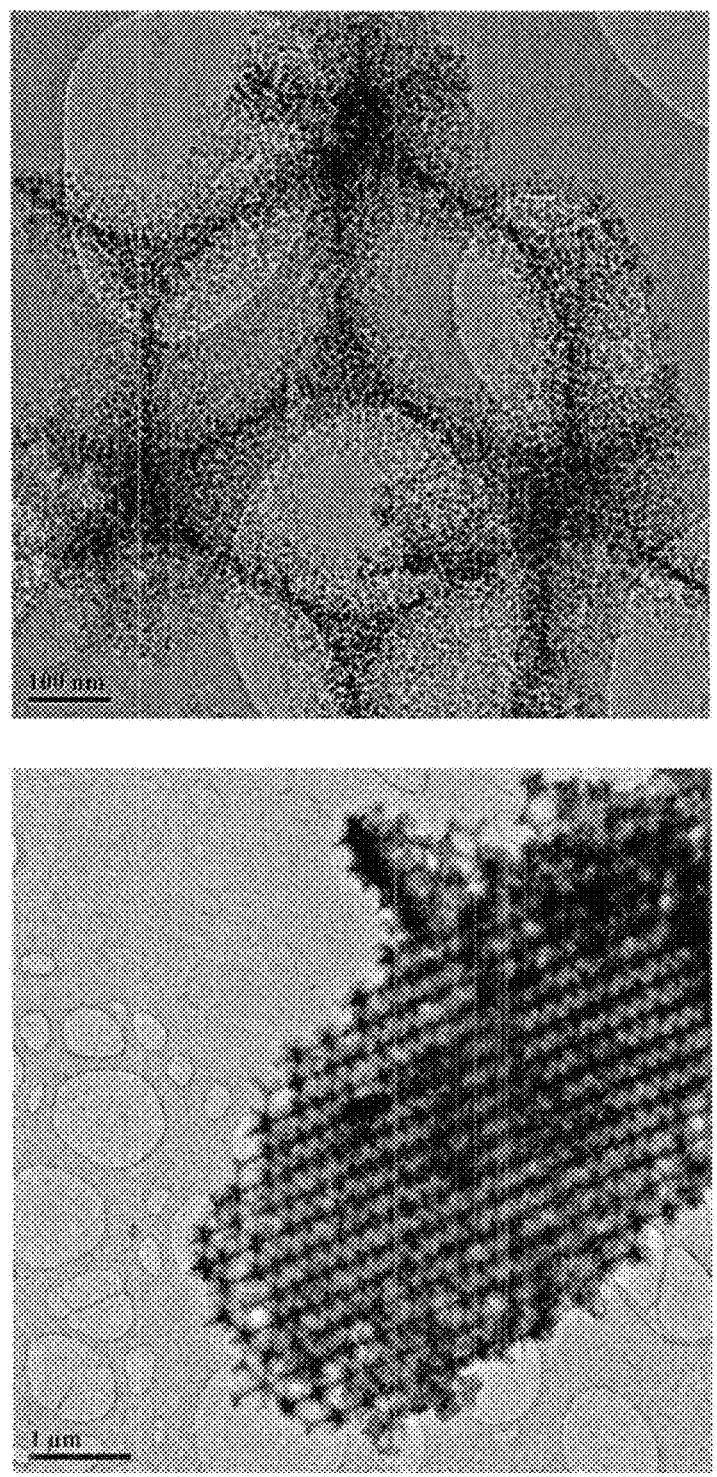
FIG. 17 shows TEM images of nanoparticle structures resulting from infiltration of a sol of molar composition 60 $SiO_2$:1.7 lysine:9500 Water:240 Ethanol, hydrolyzed at 60° C. and hydrothermally aged at 100° C., into a poly(methyl methacrylate) (PMMA) colloidal crystal.

Infiltration of Porous Structures with Silica Nanoparticle Sols for Nanocasting Particulate Materials Nanoparticle sols of EXAMPLE 6 were used to infiltrate poly(methyl methacrylate) (PMMA) colloidal crystal monoliths. Infiltration of PMMA monoliths was achieved through incipient wetness techniques, wherein small aliquots of the silica nanoparticle sols were used to periodically wet the monolith. FIG. 17 shows TEM images of the resulting packed, polyhedral aggregates and complex structures cast in the interstices of the colloidal crystal.

Example 16

Isolation of Silica Nanoparticles Through Dialysis of Lysine-Silica Sols

Approximately 3 mL aliquots of the sols of EXAMPLES 3-6 were sealed in dialysis bags (Spectra/Por® Dialysis Membrane, 3500 molecular weight cutoff (MWCO)). Dialysis was carried out over 2-5 days for each sample against approximately 1 L of distilled water under moderate to fast stirring with periodic exchange of the external dialysis solution for fresh distilled water. In the process, the pH of the dialyzed sol was reduced from its initial value (ca. 9-10) to approximately 5-6. SAXS analysis of the dialyzed sols shows relative insensitivity of particle size to the dialysis.

Example 17

Formation of Clear Silica Gels Through Ageing of Dialyzed Nanoparticle Sols

The dialyzed sols of EXAMPLE 14 were stored in sealed containers and were aged undisturbed for more than three months. The sol pH was observed to steadily increase. Clear, loose gels were formed following approximately 10 days of ageing of samples prepared by TEOS hydrolysis at room temperature (EXAMPLE 3). Sols prepared at elevated temperature, as in EXAMPLE 5, gelled after approximately 40 days, and the sols of EXAMPLE 6 appeared stable after more than three months.

Example 18

Synthesis of Clear Silica Gels by Peptide Oligomer Titration of Optically Clear Nanoparticle Sols Lysine-silica sols prepared as in EXAMPLES 3-6 were titrated with small aliquots of a 0.06 M aqueous solution of the compatible peptide oligomer di-lysine under vigorous stirring. The result of the titration in each case is a decrease in pH to a more physiologically relevant range and eventual formation of a clear gel. The amount of di-lysine required for gelation was found to decrease with increasing silica content.

Example 19

Controlling Porosity and Morphology of Clear Silica Gels by Silica Content

Figure 18:
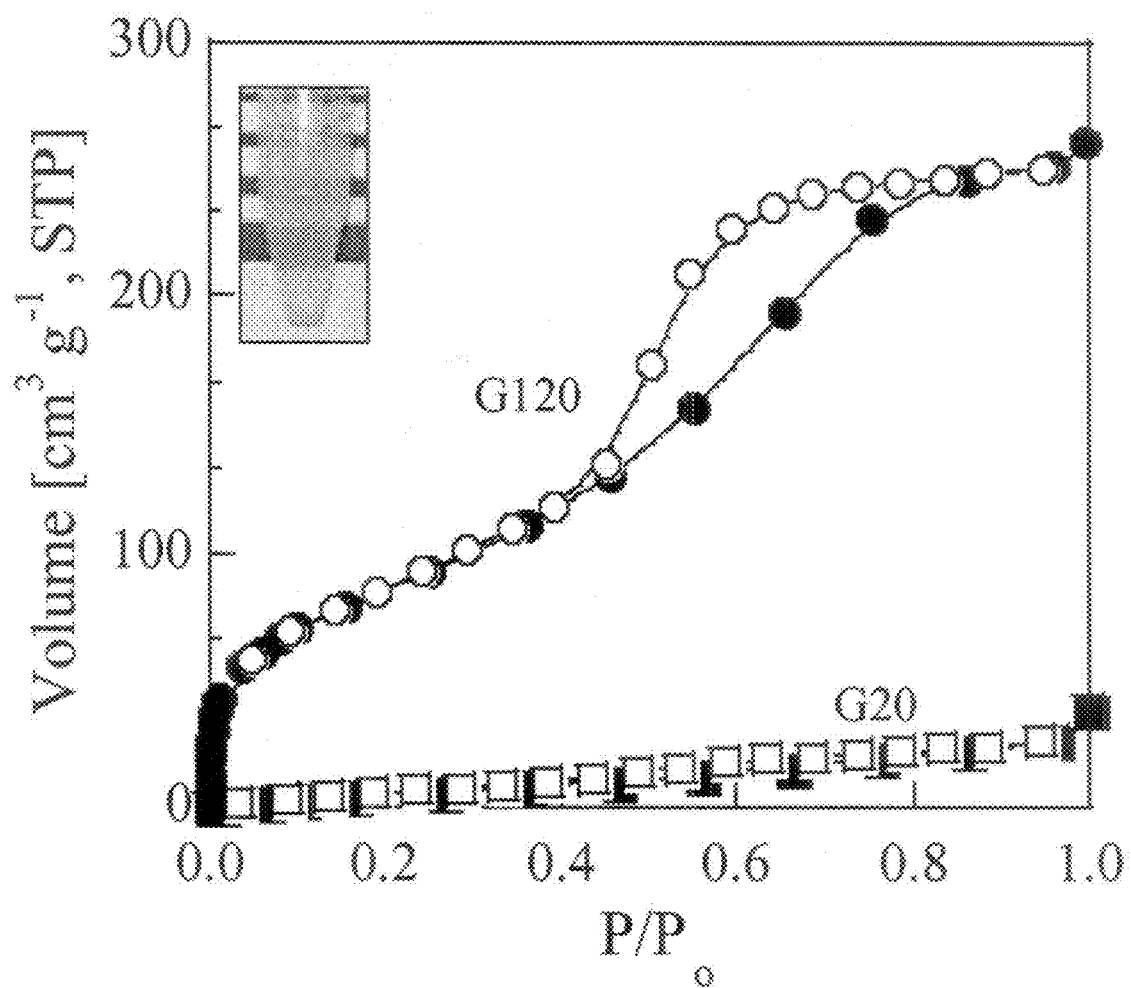
FIG. 18 shows nitrogen adsorption isotherms for gels two gels synthesized by di-lysine titration of silica-nanoparticle sols of molar composition x $SiO_2$:5.8 lysine:9500 water (x=20 (G20), 120 (G120)). The inset depicts the optically clear, well-formed gel.
Figure 19:
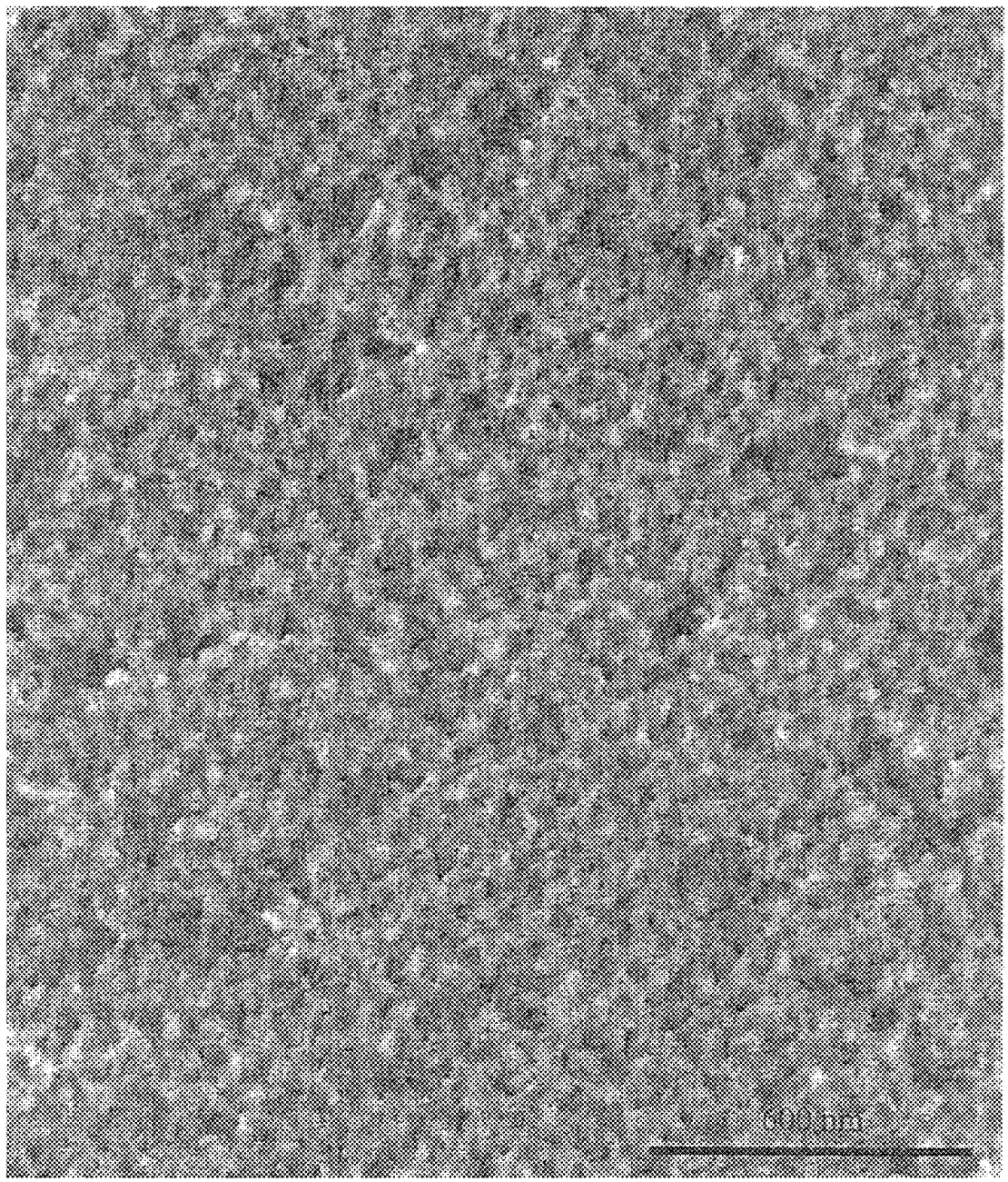
FIG. 19 shows a cryo-SEM image of a freeze-fractured gel synthesized by di-lysine titration of a lysine-silica sol of molar composition 200 $SiO_2$:5.8 Lysine:9500 $H_2O$:800 Ethanol.

Gels of EXAMPLE 16 were prepared from sols of EXAMPLE 4, having a range of silica concentrations. Formation of cryo-gels was carried out by freeze-drying these silica nanoparticle gels. Subsequent nitrogen adsorption isotherms (FIG. 18) were collected at −77° C., and reveal morphologies ranging from non-porous to ones exhibiting both micro and mesoporosity for two representative sol molar compositions x $SiO_2$:5.8 Lysine:9500$H_2O$:4x Ethanol, where x=20 (G20) and 120 (G120). FIG. 19 shows a cryo-SEM image of the freeze-fractured surface of another gel of molar silica content of x=200 following its high-pressure freezing.

Example 20

Figure 20:
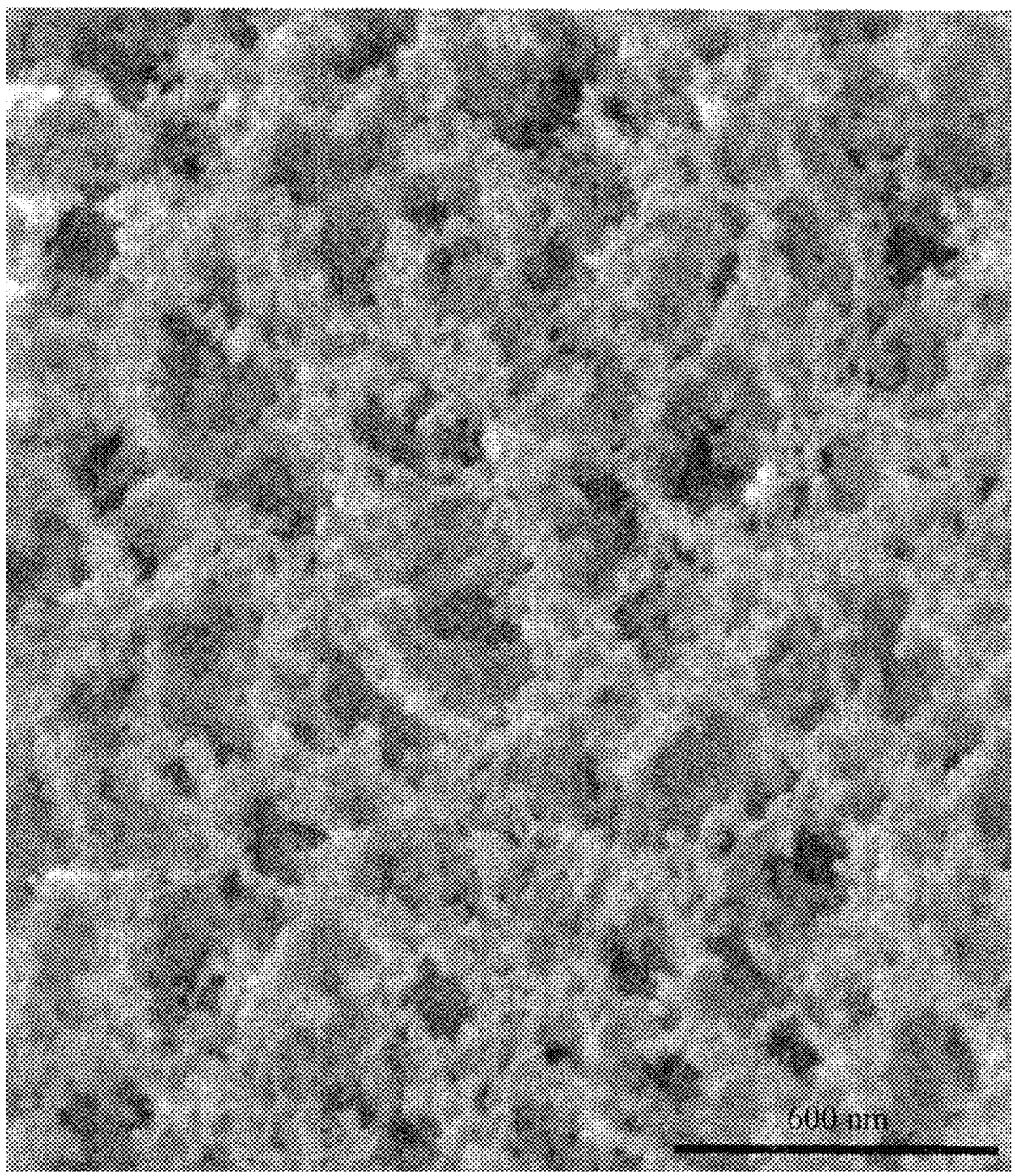
FIG. 20 shows a cryo-SEM image of a freeze-fractured gel synthesized by di-lysine titration of a lysine-silica sol of molar composition 200 $SiO_2$:5.8 Lysine:9500 $H_2O$:800 Ethanol after its 50/50 v/v dilution with biological growth medium.

Formation of Low-Density Silica Gels Via Initial Dilution with Biological Buffer Solution Sols prepared according to the procedure outlined in EXAMPLE 4 with higher silica composition (200 $SiO_2$:5.8 Lysine:9500$H_2O$:800 Ethanol) were diluted with a buffering agent (biological growth medium, MCDB131 or INS-1 Cell Medium) to a 50:50 mixture by volume. A concomitant decrease in the pH of the sol from approximately 8.8 to approximately 8.2 was measured. The compatible peptide-oligomer di-lysine was subsequently directly added to this mixture, and the mixture was vortexed for approximately 10 seconds to ensure homogenization. pH of the resulting mixture was approximately 7.5. Ageing of the mixture for 30-60 minutes resulted in a well-formed gel. Cryo-SEM images of the freeze-fractured surface of a gel prepared with INS-1 cell medium (FIG. 20) revealed a more open structure in comparison to the gels of EXAMPLE 17.

Example 21

Gel Encapsulation of Living HUVECs and INS-1 Cells 3D encapsulation of living cells was achieved with the porous gels of EXAMPLE 18. Human umbilical vein endothelial cells (Huvecs) and INS-1 insulinoma cells were encapsulated in the silica nanoparticle gels of EXAMPLE 18. Encapsulation was carried out immediately before gelation occurred. Namely, living cells were dispersed in the pre-gel mixture of EXAMPLE 18 once the mixture showed a noticeable increase in viscosity. The cells suspended in the gel were transferred to 2-well NUNC chambers and incubated for approximately 4 hours to ensure setting of the gel and its adherence to the sides and bottom of the vessel. Growth medium was then added to the surface of the gels, and the samples were again incubated at 37° C. in a 5% $CO_2$ environment. Growth medium was changed every two days. Growth medium spiked with labeled glucose was administered throughout time-series experiments, and subsequent NMR analysis of the medium after 24 hours of contact with the gel-encapsulated cells showed glucose metabolites up to 3 days, confirming the sustained viability of the cells. Additionally, the LIVE/DEAD viability assay (Invitrogen, L-3224) was also employed to stain living and dead cells with subsequent fluorescence confocal laser scanning microscopy (LSCM) employed to assess/confirm cell viability.

Example 22

Cell Patterning on Substrates with Periodic Banded Silica Coatings

Figure 21:
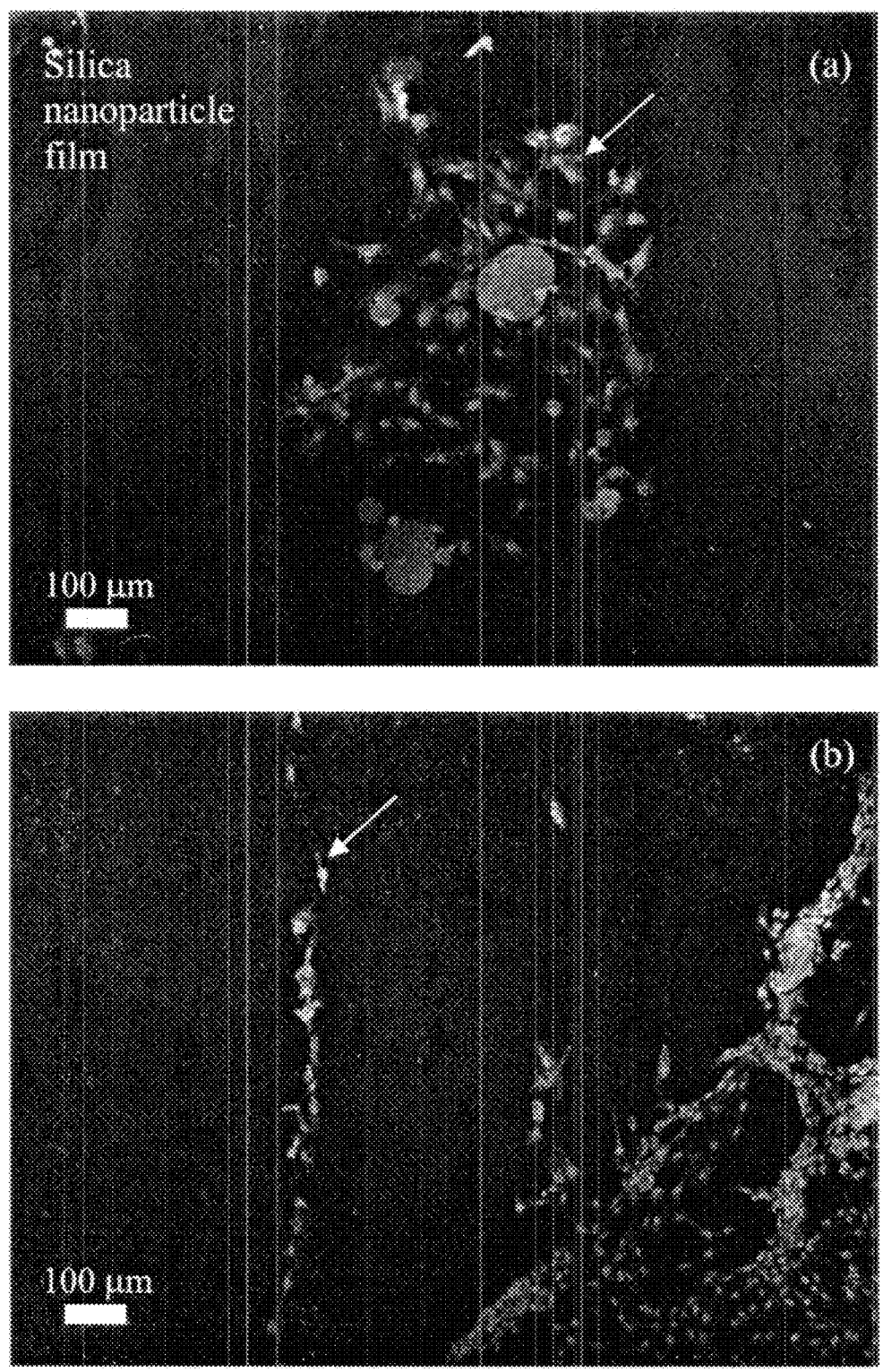
FIG. 21 shows laser scanning confocal microscopy images of human umbilical cord endothelial cells (HUVECs) growing only in regions of a glass coverslip that are not coated by a silica nanoparticle film. Image (a) shows a cluster of cells (arrow) attached directly to the glass coverslip, exposed by a hole in the silica nanoparticle film. Image (b) shows the patterned alignment of cells (arrow) along a banded region on which no silica nanoparticle coating is observed.

Human umbilical vein endothelial cells (HUVECs) were seeded on uniformly coated and periodically-banded silica nanoparticle films of EXAMPLES 13-14. Following incubation at 37° C. for a period of nine days, cells were fixed via incubation for 15 minutes with paraformaldehyde. The films of cells were subsequently washed three time with fluorescence buffer, and incubated for an additional 15 minutes with a membrane and nuclear staining assay (Image-iT Live Plasma Membrane and Nuclear Labeling Kit, Invitrogen, 134406) consisting of a cell membrane permeable blue-fluorescent Hoechst 33342 dye at a concentration of 2.0 μmole $mL^{-1}$, and a cell membrane red-fluorescent Alexa Fluor® 594 wheat germ aggutin (WGA) dye at 5.0 mole $mL^{-1}$ concentration in fluorescence buffer. Following three additional washings using fluorescence buffer, mounting medium was used to fix a the sample to either a coverslip or microscope slide, and the sample was dried for two days before sealing the edges. Fluorescence laser scanning microscopy was then employed for cell imaging. FIG. 21a shows a cluster of cells localized in a break in the silica nanoparticle film, a consistently observed phenomenon among all samples of lack of cell adhesion to silica nanoparticle coated surfaces. FIG. 21b shows the patterning of cells in a single file line as a result of a uniform, line-shaped break in the silica nanoparticle film.

Example 23

Figure 22:
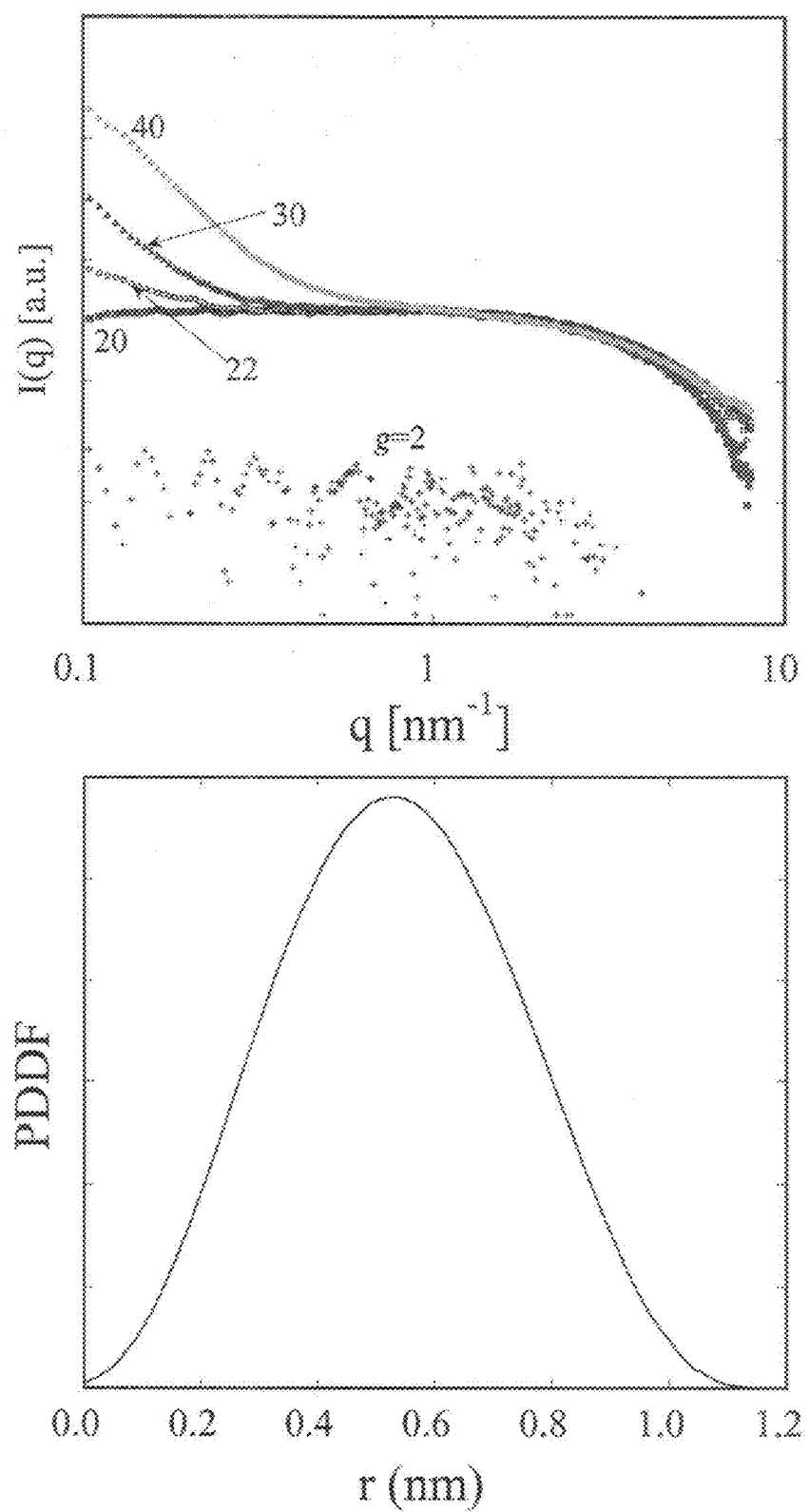
FIG. 22 shows (top) the evolution of SAXS patterns as a function of germania content for sols having composition g $GeO_2$:5.8 lysine:9500$H_2O$:4 g ethanol. The PDDF (bottom) extracted from the scattering curve for the g=20 sol indicates the presence of nanoparticles on the order of 1 nm in diameter.

Benign Synthesis of Germania Nanoparticles Through Hydrolysis of Germanium (IV) Tetraethoxide (GTE) in Aqueous Lysine Solutions Based on the methods of EXAMPLES 3-6, germania nanoparticles of approximately 1 nm in diameter were synthesized in aqueous lysine solutions by hydrolysis of germanium (IV) tetraethoxide (GTE) in lieu of TEOS. Germanium (IV) tetraethoxide (GTE, 99.95%, Aldrich), L-lysine (Sigma), and purified water were combined to give molar compositions g $GeO_2$:x lysine:9500$H_2O$:4 g ethanol where $0 \leq g \leq 60$ and x=0, 5.8. In addition to large (ca. 100 nm) germania crystals, germania nanoparticles in the presence of lysine were also detected by SAXS once the germania solubility limit was surpassed (i.e., g~20) as shown by the SAXS patterns and resulting nanoparticle PDDF in FIG. 22.

Example 24

Figure 23:
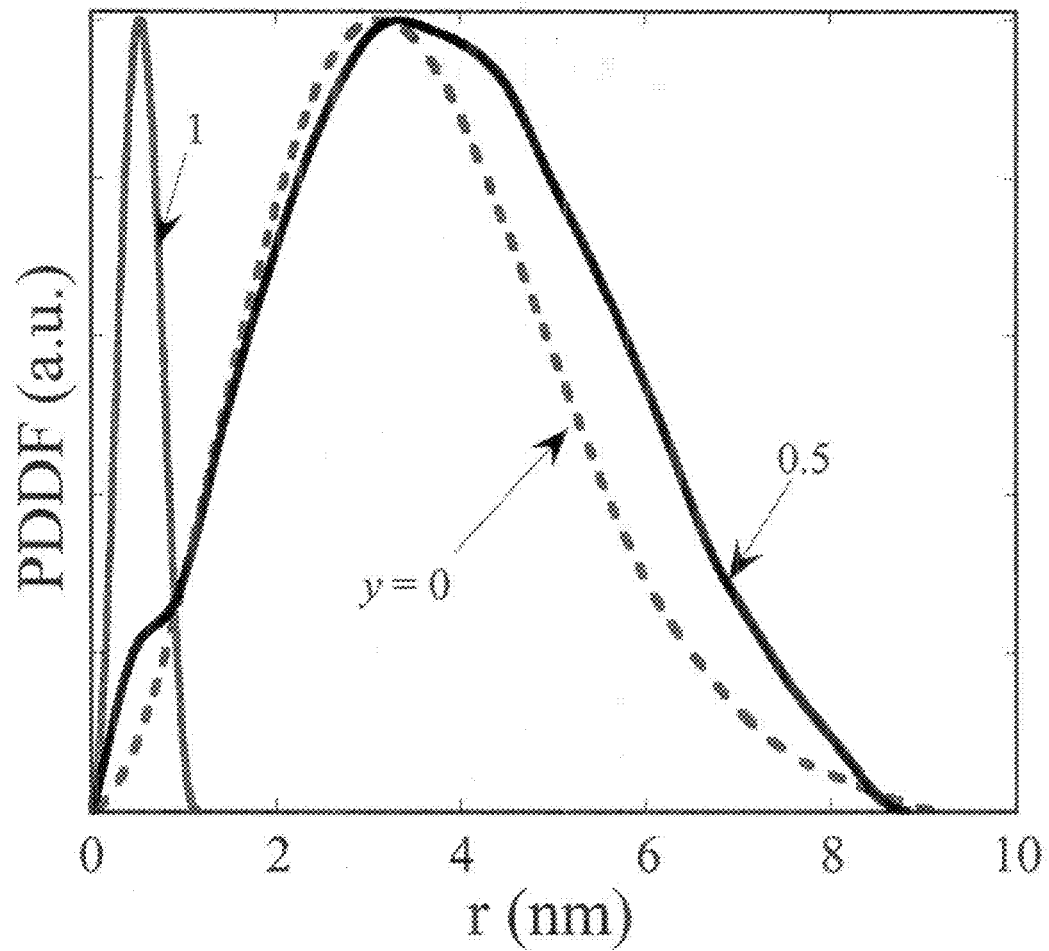
FIG. 23 shows PDDF extracted for SAXS analysis of germania and silica sols, hydrolyzed simultaneously, of molar composition 20y $GeO_2$:20(1−y) $SiO_2$:5.8 lysine:9500$H_2O$: 80 ethanol where y=0, 0.50, and 1.0.

Benign Synthesis of Silica and Germania Nanoparticles Through Simultaneous Hydrolysis of TEOS and GTE in Aqueous Lysine Solutions Mixtures containing both silica and germania nanoparticles were prepared by first combining GTE with TEOS at prescribed Si/Ge molar ratios with subsequent addition of an aqueous lysine solution to give molar compositions 20y $GeO_2$:20(1−y) $SiO_2$:5.8 lysine:9500$H_2O$:80 ethanol where y=0, 0.09, 0.33, 0.50, and 1.0. Complete hydrolysis of GTE and TEOS was carried out under vigorous stirring at room temperature for approximately 20 hours. FIG. 23 shows the PDDF extracted for three representative Si/Ge ratios. The shoulder in the PDDF at small radius for the case of Si/Ge=1 (i.e., y=0.5) is indicative of the coexistence of small germania nanoparticles (c.a., 1 nm) and larger silica nanoparticles (c.a., 8 nm) of sizes concomitant with nanoparticles observed in pure germania (i.e., y=0) and pure silica (i.e., y=1) syntheses.

Example 25

Figure 24:
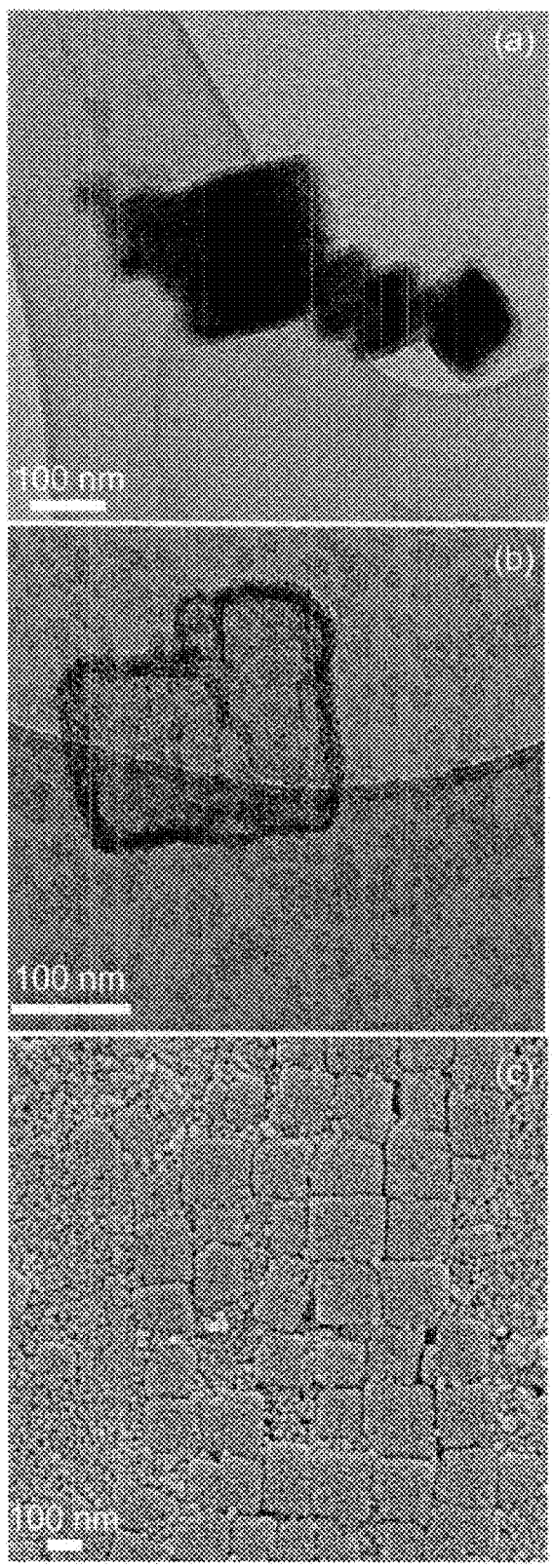
FIG. 24 shows the formation of hollow silica nanoparticle capsules from germania and silica sols, hydrolyzed simultaneously, of molar composition 40 $GeO_2$:60 $SiO_2$:5.8 lysine: 9500$H_2O$:400 ethanol. TEM images from (a) before and (b) after dialysis reveal a silica nanoparticle coating of cubic germania particles and a hollow shell, respectively. Panel (c) shows an SEM image of the dialyzed sol, revealing the structure of the hollow shells.

Benign Synthesis of Hollow Silica Nanoparticle Capsules
Room temperature assembly of silica nanoparticles on the surface of germania crystals was achieved through aging of sols of EXAMPLE 24 of molar composition 40 $GeO_2$:60 $SiO_2$:5.8 lysine:9500$H_2O$:400 ethanol. Subsequent dissolution of the germania crystals was carried out by placing approximately 3 mL of the sol into dialysis bags (Spectra/Por® Dialysis Membrane, 3500 molecular weight cutoff (MWCO)). Dialysis was carried out over 2-5 against approximately 1 L of distilled water under moderate to fast stirring with periodic exchange of the external dialysis solution for fresh distilled water. TEM images of dried particles before dialysis (e.g., FIG. 24a) reveal a silica nanoparticle shell around core cubic germania crystals. TEM and SEM images of dried particles following dialysis (e.g., FIGS. 24b and 24c) reveal a hollow shell composed of associated nanoparticles.

Example 26

Benign Synthesis of Aluminum-Substituted Silica Nanoparticles Through Simultaneous Hydrolysis of TEOS and Aluminum Triethoxide in Aqueous Lysine Solutions
Aluminum-substituted silica nanoparticles were synthesized at room temperature through simultaneous hydrolysis of TEOS and aluminum triethoxide in aqueous lysine solutions. Nanoparticles were prepared via reaction solutions of starting molar compositions x TEOS: y Al($OC_2H_5$)$_3$:5.8 Lysine:9500$H_2O$, with a Si/Al ratio, x/y, ranging from 50 to 200 and total $Si^+$ Al molar compositions (x+y) of 20 and 60. The prescribed amount of aluminum triethoxide was added to TEOS, and the mixture was stirred for approximately 10 minutes. Lysine in a small aliquot of water was added to the mixture and stirred for approximately 30 minutes, after which distilled water was added to reach the desired molar composition. Hydrolysis was carried out under vigorous stirring for a period of approximately 24 hours. SAXS analysis confirmed the formation of nanoparticles.

Example 26

Nanoparticle Formation in the Presence of Arginine
Silica nanoparticles were prepared at room temperature with arginine acting as the basic amino acid in lieu of the lysine-mediated synthesis of EXAMPLE 3. Optically clear aqueous sols of L-arginine, tetraethylorthosilicate (TEOS), and water of molar composition of 6.8 $SiO_2$:152.5 Arginine:9500$H_2O$:27.2 Ethanol were prepared by first mixing arginine with distilled water. Subsequent addition of the prescribed amounts of TEOS carried out under vigorous stirring for at least 24 hours ensured complete hydrolysis. The resulting sol was higher in pH, at approximately 10.5, than the lysine-silica sols described in EXAMPLE 3. SAXS analysis shows that the resulting nanoparticles are smaller than 4 nm in diameter, consistent with amino-acid-mediated pH affects on particle size described in EXAMPLE 8.

Additional Embodiments

A number of embodiments have been described. Nevertheless, it will be understood that various modifications may be made without departing from the spirit and scope of the invention. For example, in addition to silica formation, other metal oxides hold exciting potential for applications spanning the biological to general materials community. For instance, germania has been identified as an active mineral participating in biogenic systems. Rimer et al. [Rimer, J. D., et al., (2007) Langmuir. 23, 2784-2791] recently explored the formation of germania nanoparticles in highly alkaline mixtures containing various common zeolite structure directing agents, and highlighted similarities between the phase behavior of germania and silica sols under those conditions.

Along these lines, the benign methods disclosed herein can be more broadly applicable for hydrolysis of other metal ethoxides, and the subsequent directed formation of metal oxide nanoparticles. For example, EXAMPLE 23, supra, describes the ability to employ the simple and benign hydrolysis conditions disclosed herein for synthesis of the oxide of germanium (i.e., germania) via hydrolysis of germanium (IV) tetraethoxide (GTE). In addition to nanoscale germania crystals formed upon rapid hydrolysis in the absence and presence of lysine, germania nanoparticles on the order of 1 nm in diameter form in aqueous lysine solutions. Moreover, it is possible to simultaneously hydrolyze TEOS and GTE in a common aqueous lysine solution. The resulting parallel production of silica and germania nanoparticles is described, for example, in EXAMPLE 24, supra.

In the sols derived from simultaneous hydrolysis of germania and silica sources, silica nanoparticle association at the periphery of germania crystals and subsequent dissolution of the germania crystals through aqueous dilution (i.e., dialysis) can also lead to the benign formation of hollow silica nanoparticle shells. EXAMPLE 24, for example, describes a process by which silica nanoparticle-based capsules can be synthesized.

Based on the enhanced reactivity of germania upon incorporation within silica-based zeolite structures, such simultaneous hydrolysis of germania and silica presents interesting implications for benign catalyst synthesis in the future. In some embodiments, aluminum-substituted silicate nanoparticles can be synthesized via simultaneous hydrolysis of TEOS and aluminum triethoxide in aqueous lysine solutions. EXAMPLE 26, for example, describes a process by which such nanoparticles of controllable size can be synthesized.

In some embodiments (see, e.g., EXAMPLE 27, supra), substitution of other basic amino acids for lysine is possible for room temperature synthesis of silica nanoparticles. In particular, arginine performs similar to lysine when included in an aqueous mixture with silica. Namely, SAXS analysis has also detected nanoparticles formed in the presence of arginine.

Other embodiments are in the claims.

What is claimed is:
1. A method for forming metal oxide nanoparticles, comprising:
preparing a solution of water and a basic amino acid; and
adding a metal oxide precursor to the solution under conditions which result in the formation of the metal oxide nanoparticles from a reaction between the metal oxide precursor and water in the solution of the water and the basic amino acid,
wherein the amino acid is a simple amino acid, and
the solution has a pH in a range from 8.5 to 11.
2. The method of claim 1, wherein the nanoparticle solution obtained is further aged at elevated temperature to provide for metal oxide nanoparticles have an average maximum dimension of 10 nm.

3. The method of claim 1, wherein the conditions include elevated temperatures of up to 60° C., to provide for metal oxide nanoparticles that have an average dimension of 5 nm or less.

4. The method of claim 1, wherein the conditions comprise maintaining the mixture at a temperature of 100° C. during formation of the metal oxide nanoparticles.

5. The method of claim 1, wherein the conditions comprise stirring or agitating the mixture for one hour or more during formation of the metal oxide nanoparticles.

6. The method of claim 1, wherein the metal oxide nanoparticles are silica nanoparticles.

7. The method of claim 1, wherein the metal oxide nanoparticles are germania or alumino-silicate nanoparticles.

8. The method of claim 1, wherein the basic amino acid is lysine or arginine.

9. The method of claim 1, wherein the metal oxide precursor is a silica precursor.

10. The method of claim 9, wherein the silica precursor is TEOS.

11. The method of claim 1, wherein the water comprises deuterated water.

12. The method of claim 1, further comprising forming a gel comprising the metal oxide nanoparticles.

13. The method of claim 12, wherein the gel is formed by adding poly peptide to the sol.

14. The method of claim 13, wherein the poly peptide is di-lysine (Lysine-Lysine).

15. A method of encapsulating living cells, comprising:
    forming metal oxide nanoparticles according to the method of claim 1;
    lowering the pH to a physiological level by adding dilysine;
    adding living cells and growth medium to the solution prior to nanoparticle gelation; and
    allowing gelation to occur,
thereby encapsulating the living cells with the metal oxide nanoparticles.

16. The method of claim 15, wherein the cells are mammalian cells.

17. The method of claim 1, further comprising casting a film comprising the metal oxide nanoparticles on a support.

* * * * *

UNITED STATES PATENT AND TRADEMARK OFFICE
CERTIFICATE OF CORRECTION

PATENT NO. : 8,263,035 B2  
APPLICATION NO. : 11/925299  
DATED : September 11, 2012  
INVENTOR(S) : Tracy M. Davis et al.

Page 1 of 1

It is certified that error appears in the above-identified patent and that said Letters Patent is hereby corrected as shown below:

Column 23, line 3 in Claim 3, after "average" insert --maximum--.

Signed and Sealed this  
Sixth Day of November, 2012

David J. Kappos  
*Director of the United States Patent and Trademark Office*